US008496961B2

(12) United States Patent
Hong et al.

(10) Patent No.: US 8,496,961 B2
(45) Date of Patent: Jul. 30, 2013

(54) DELIVERY OF NUCLEIC ACID-LIKE COMPOUNDS

(75) Inventors: Keelung Hong, San Francisco, CA (US); Wei-Wen Zheng, Las Vegas, NV (US); Daryl C. Drummond, Concord, CA (US); Dmitri B. Kirpotin, San Francisco, CA (US); Mark Eamon Hayes, San Francisco, CA (US)

(73) Assignee: Sutter West Bay Hospital, San Francisco, CA (US)

( * ) Notice: Subject to any disclaimer, the term of this patent is extended or adjusted under 35 U.S.C. 154(b) by 1973 days.

(21) Appl. No.: 10/439,856

(22) Filed: May 15, 2003

(65) Prior Publication Data
US 2004/0037874 A1    Feb. 26, 2004

Related U.S. Application Data

(60) Provisional application No. 60/381,417, filed on May 15, 2002.

(51) Int. Cl.
*A61K 9/127* (2006.01)

(52) U.S. Cl.
USPC ............ 424/450; 424/489; 424/490; 264/4.1

(58) Field of Classification Search
USPC ........................... 424/450, 489, 490; 264/4.1
See application file for complete search history.

(56) References Cited

U.S. PATENT DOCUMENTS

| | | | |
|---|---|---|---|
| 4,897,355 | A | 1/1990 | Eppstein et al. |
| 5,171,678 | A | 12/1992 | Behr et al. |
| 5,279,833 | A | 1/1994 | Rose |
| 5,283,185 | A | 2/1994 | Epand et al. |
| 5,415,867 | A | 5/1995 | Minchey et al. |
| 5,556,637 | A | 9/1996 | Hager et al. |
| 5,705,385 | A | 1/1998 | Bally et al. |
| 5,753,262 | A * | 5/1998 | Wyse et al. .................. 424/450 |
| 5,885,613 | A | 3/1999 | Holland et al. |
| 5,962,429 | A | 10/1999 | Welsh et al. |
| 5,972,380 | A | 10/1999 | Daleke |
| 5,972,600 | A | 10/1999 | Szoka, Jr. et al. |
| 5,976,567 | A | 11/1999 | Wheeler et al. |
| 5,980,935 | A | 11/1999 | Kirpotin et al. |
| 5,981,501 | A | 11/1999 | Wheeler et al. |
| 5,994,317 | A | 11/1999 | Wheeler |
| 6,060,316 | A | 5/2000 | Young et al. |
| 6,086,913 | A | 7/2000 | Tam et al. |
| 6,096,335 | A | 8/2000 | Thierry |
| 6,110,745 | A | 8/2000 | Zhang et al. |
| 6,120,798 | A | 9/2000 | Allen et al. |
| 6,210,707 | B1 | 4/2001 | Papahadjopoulos et al. |
| 6,287,591 | B1 | 9/2001 | Semple et al. |
| 6,333,433 | B1 | 12/2001 | Banerjee et al. |
| 6,342,244 | B1 | 1/2002 | Zalipsky |
| 6,365,179 | B1 | 4/2002 | Zalipsky et al. |
| 2002/0034551 | A1 | 3/2002 | Jones et al. |

FOREIGN PATENT DOCUMENTS

| | | |
|---|---|---|
| WO | WO 93/05162 | 3/1993 |
| WO | WO 96/40964 | 12/1996 |
| WO | WO 98/20857 | 5/1998 |
| WO | WO 98/51278 | 11/1998 |
| WO | WO 98/58630 A1 | 12/1998 |
| WO | WO 99/33493 | 7/1999 |
| WO | WO 00/03683 | 1/2000 |
| WO | WO 00/15825 | 3/2000 |
| WO | WO 00/71096 | 11/2000 |
| WO | WO 01/05374 A1 | 1/2001 |
| WO | WO 01/15726 | 3/2001 |
| WO | WO 01/93836 | 12/2001 |

OTHER PUBLICATIONS

Antopolsky et al., Peptide-oligonucleotide phosphorothioate conjugates with membrane translocation and nuclear localization properties, *Bioconjugate Chem.* 10:598-606 (1999).
Behr, et al., Gene transfer with synthetic cationic amphiphiles: prospects for gene therapy, *Bioconjugote Chem.* 5:382-389 (1994).
Boulikas et al., Histones, protamine, and polylysine but not poly(E:K) enhance transfection efficiency *Int. J. Oncology* 10:317-322 (1997).
Branden et al., A peptide nucleic acid-nuclear localization signal fusion that mediates nuclear transport of DNA. *Nature Biotechnology* 17:784-787 (1999).
Cohen, et al. Sustained delivery and expression of DNA encapsulated in polymeric nanoparticles. *Gene Therapy* 7:1896-1905 (2000).
Drummond et al., Synthesis and characterization of N-acylated, pH-sensitive 'caged' aminophospholipids. *Chem. Phys. Lipids* 75:27-41(1995).
Drummond et al., Current status of pH-sensitive liposomes in drug delivery. *Progress in Lipid Research*, 39:409-60 (2000).
Fasbender, et al., Complexes of adenovirus with polycationic polymers and cationic lipids increase the efficiency of gene transfer in vitro and in vivo. *J. Biol. Chem.* 272:6479-6489 (1997).
Gaber et al., Thermosensitive Sterically stabilized liposomes: formulation and in vitro studies on mechanism of doxorubicin release by bovine serum and human plasma. Pharm. Res. 12:1407-16 (1995).

(Continued)

*Primary Examiner* — Gollamudi Kishore
(74) *Attorney, Agent, or Firm* — Foley & Lardner LLP

(57) ABSTRACT

A process for preparing a microparticulate complex is provided. The process comprises (a) combining a particle-forming component ("PFC") and a nucleic acid-like component ("NAC") in a monophasic composition comprising water and a water-miscible, organic solvent to form a mixture wherein the PFC and the NAC are independently molecularly or micellarly soluble in the aqueous/organic solvent system, and (b) reducing the amount of the organic solvent in the mixture. This effects formation of the microparticulate complex of the NAC and the PFC. Also provided is a microparticulate complex that comprises a particle-forming component complexed to a nucleic acid-like component forming an approximately spherical particle, wherein the particle-forming component encloses an interior of the particle containing the nucleic acid-like component and the so-enclosed interior volume has less than about 50% (preferably less than 20%) of the volume containing free water.

2 Claims, 3 Drawing Sheets

OTHER PUBLICATIONS

Gaber et al., Thermosensitive liposomes: extravasation and release of contents in tumor microvascular networks. *Int. J. Radiat. Oncol Biol. Phys* 36:1177-1187 (1996).

Glushakova et al., The fusion of artificial lipid membranes induced by the synthetic arenavirus 'fusion peptide'. *Biochim. Biophys. Acta* 1110:202-208 (1992).

Hawley-Nelson et al., Lipofectamine reagent a new, higher efficiency polycationic liposome transfection reagent, *Focus* 15(3):73(1993).

Hodgson et al., Virosomes: cationic liposomes enhance retroviral transduction. *Nature Biotechnology* 14:339-342 (1996).

Hoganson, et al. Targeted delivery of DNA encoding cytotoxic proteins through high-affinity fibroblast growth factor receptors. *Human Gene Therapy* 9:2565-2575 (1998).

Jain et al., Estradiol enhances gene delivery to human breast tumor cells. *J. Mol. Medicine* 76:709-714 (1998).

Kaiser and Toborek, Liposome-niediated high-efficiency transfection of human endothelial cells. *J. Vascular Res* 38:133-43 (2001).

Kamata et al, Amphiphilic peptides enhance the efficiency of liposome-mediated DNA transfection. Nucleic Acids Research vol. 22. No. 3 (1994).

Kichler et al., Influence of membrane-active peptides on lipospermine/DNA complex mediated gene transfer. *Bioconjugate. Chem* 8:213-221 (1997).

Kirpotin et al., Liposomes with detachable polymer coating: destabilization and fusion of dioleoylphosphatidylethanolamine vesicles triggered by cleavage of surface-grafted poly(ethylene glycol). *FEBS Lett* 388:115-118 (1996).

Kong et al., Efficacy of liposomes and hyperthermia in a human tumor xenograft model: importance of triggered drug release. *Cancer Res* 60:6950-6957 (2000).

Lambert, et al. Polyisobutylcyanoacrylate nanocapsules containing an aqueous core for the delivery of oligonucleotides. *Int. J. Pharmaceutics* 214:13-16 (2001).

Lee et al., Folate-targeted, anionic liposome-entrapped polylysine-condensed DNA for tumor cell-specific gene transfer *J. Biol. Chem.* 271:8481-8487 (1996).

Lerman, A transition to a compact form of DNA in polymer solutions *Proc. Natl Acad. Sci. USA* 68:1886-1890 (1971).

Leroux et al., N-isopropylacrylamide copolymers for the preparation of pH-sensitive liposomes and polymeric micelles. *J. Controlled Release* 72:71-84 (2001).

Leventis et al., Interactions of mammalian cells with lipid dispersions containing novel metabolizable cationic amphiphiles. *Biochim. Biophys. Acta* 1023:124-32 (1990).

Li et al., In vivo gene transfer via intravenous administration of cationic lipid-protamine-DNA (LPD) complexes *Gene Therapy* 4:891-900 (1997).

Louie et al., Quantification of the effect of excluded volume on double-stranded DNA. *J. Mol. Biol.* 242:547-558 (1994).

Maurer, et al. Spontaneous Entrapment of Polynucleotides upon Electrostatic Interaction with Ethanol-Destabilized Cationic Liposomes, *Biophys J*. 80:2310-2326 (2001).

Murphy, et al. Development of an effective gene delivery system: a study of complexes composed of a peptide-based amphiphilic DNA compaction agent and phospholipid. *Nucleic Acid Res*. 29:3694-3704 (2001).

Needham et al., The development and testing of a new temperature-sensitive drug delivery system for the treatment of solid tumors. *Adv. Drug Delivery. Rev.* 53:285-305 (2001).

Pouton, Nuclear import of polypeptides, polynucleotides and supramolecular complexes *Adv. Drug. Del. Rev* 34:51-64 (1998).

Puyal et al., A new cationic liposome encapsulating genetic material. A potential delivery system for polynucleotides. *Eur. J. Biochem.* 228:697-703 (1995).

Reddy et al., Enhanced folate receptor mediated gene therapy using a novel pH-sensitive lipid formulation. *J. Controlled Release* 64:27-37 (2000).

Rosenecker et al.,Increased liposome extravasation in selected tissues: effect of substance P. *Proc. Natl. Acad. Sci. USA*, 93:7236-7241 (1996).

Rui et al., Diplasmenylcholine—folate liposomes: an efficient vehicle for intracellular drug delivery. *J. Am. Chem. Soc.* 120:11213-11218 (1998).

Saalman et al, Effect of 2.45 GHz microwave radiation on permeability of unilamellar liposomes to 5(6)-carboxyfluorescein. Evidence of non-thermal leakage. *Biochnn. Biophys. Acta* 1064:124-130 (1991).

Schuber, "Chemistry of ligand-coupling to liposomes", in: *Liposomes as Tools for Basic Research and Industry*, ed. by J.R. Philippot and F. Schuber, CRC Press, Boca Raton, 1995, p. 21-37.

Sebestyen et al., DNA vector chemistry: the covalent attachment of signal peptides to plasmid DNA. *Nature Biotechnology* 16:80-85 (1998).

Semple, et al., Efficient Encapsulation of Antisense Oligonucleotides in Lipid Vesicles Using Ionizable Aminolipids: Farmation of Novel Small Multilamellar Vesicle Structures, *Biochim Biophys Acta* 1510:152-166 (2001).

Simoes et al., Mechanisms of gene transfer mediated by lipoplexes associated with targeting ligands or pH-sensitive peptides. *Gene Therapy* 6:1798-1807 (1999).

Solodin et al. A novel series of amphiphilic imidazolinium compounds for in vitro and in vivo gene delivery. *Biochemistry* 34:13537-13544 (1995).

Sorgi et al. Protamine sulfate enhances lipid-mediated gene transfer. *Gene Therapy* 4:961-968 (1997).

Stamatatos et al., Interactions of cationic lipid vesicles with negatively charged phospholipid vesicles and biological membranes. *Biochemistry* 27:3917-3925 (1988).

Thompson et al., Triggerable plasmalogen liposomes: improvement of system efficiency. *Biochim. Biophys. Acta* 1279:25-34 (1996).

Wagner, Application of membrane-active peptides for nonviral gene delivery. *Adv. Drug Delivery Rev* 38:279-289 (1999).

Wang, et al. Encapsulation of plasmid DNA in biodegradable poly(D, L-lactic-co-glycolic acid) microspheres as a novel approach for immunogene delivery. *J. Controlled Release* 57:9-18 (1999).

Xu, et al. Physicochemical characterization and purification of cationic lipoplexes. *Biophys. J*. 77:341-353 (1999).

Yatvin et al., Design of liposomes for enhanced local release of drugs by hyperthermia. *Science* 202:1290-3 (1978).

Zanta et al., Gene delivery: a single nuclear localization signal peptide is sufficient to carry DNA to the cell nucleus. *Proc. Natl. Acad. Sci. USA* 96:91-96 (1999).

Reddy et al, Folate-targeted, cationic liposome-mediated gene transfer into disseminated peritoneal tumors. *Gene Therapy* 9:1542-50 (2002).

* cited by examiner

DELIVERY OF NUCLEIC ACID-LIKE COMPOUNDS

RELATED APPLICATIONS

This application claims priority to U.S. Provisional Patent Application No. 60/381,417 filed on May 15, 2002, the entire disclosure of which is incorporated herein by reference.

FIELD OF THE INVENTION

The present invention relates to biotechnology, human and veterinary medicine, particularly to the methods and compositions for delivery of nucleic acid-like components to living cells.

BACKGROUND OF THE INVENTION

Introducing nucleic acids into living cells is an important process in modern biological research, industry, and medicine. Efficient delivery of a functional nucleic acid into a living cell is an indispensable component of genetic engineering, recombinant protein production, and medical technologies known as gene therapy.

For example, gene therapy involves the transfer of normal, functional genetic material into specific cells to correct an abnormality due to a deficient or defective gene product. A variety of methods have been developed to facilitate both in vivo, in vitro, or ex vivo gene transfer. One of the most frequently used delivery systems for achieving gene therapy involves viral vectors, most commonly adenoviral and retroviral vectors. However, the viral vectors have inherent problems including immunogenic and inflammatory responses, limited size of expression cassettes, possibility of viral infection or permanent viral gene integration. Non-viral delivery systems, for example, cationic liposomes and polycations, provide alternative methods which generally do not possess the disadvantages of viral vectors.

Alternatively, gene therapy involves the transfer of natural or synthetic oligonucleotides and polynucleotides into normal and/or pathological cells with the purpose of correcting or eliminating the diseased cells. For example, antisense oligonucleotides are used to block undesirable pathways of protein expression in the cells. Polynucleotide inductors of immunity, such as poly(I, C) or oligo- and polynucleotides having methylated GC pairs are used to increase the patients' defense against pathogens such as viruses or cancer cells. Ribozymes are nucleic acids that catalyze selective degradation of other polynucleotides in the diseased cells, for example, in cancer or virus-infected cells. Because oligo- and polynucleotides generally have low permeability through cell membranes, and are quickly eliminated from the body, there is the need for oligo/polynucleotide delivery vehicles that would allow enhanced intracellular delivery and protection from degradation and/or elimination from the body.

In theory, the positively charged liposomes can complex to the negatively charged nucleic acids, for example, plasmids, via electrostatic interactions. To date many publications demonstrate that liposome-plasmid DNA complexes can mediate efficient transient expression of a gene in cultured cells but poor in vivo transfection efficiencies. Unlike viral vector preparations, liposome-DNA complexes are insufficiently stable in regard to their size or activity, and thus unsuitable for systemic injection. A large excess of cationic lipids is frequently used in these formulations, and contributes considerable toxicity to target cells.

In the past, methods based on detergent dialysis and extrusion have produced small lipid-DNA particles. Other methods of preparing lipid-DNA particles are based on solvent extraction of cationic lipid-neutralized DNA in lipid-soluble solvent from an immiscible two-phase system, with subsequent hydration and either extrusion or sonication of the solvent-free complexes to reduce the size. Although these preparations can be prepared by including neutral lipids and/or hydrophilic polymer derivatized lipid for prolonging such particle in circulation, in vivo transfection activities of such preparations are low.

It would be desirable to have methods and materials that can be scaled up easily for manufacture and that can produce nucleic acid-carrying particles that are small, active, and biocompatible.

Nucleic acid complexes for gene delivery are generally known in the art.

Wheeler et al., U.S. Pat. Nos. 5,976,567 and 5,981,501 disclose preparation of serum-stable plasmid-lipid particles by contacting an aqueous solution of a plasmid with an organic solution containing cationic and non-cationic lipids to provide a clear single phase. The clear single phase of Wheeler et al. encompasses organic phases in which aqueous component is present in a microemulsion form ("reverse phase" methods).

Thierry et al., U.S. Pat. No. 6,096,335 disclose preparing of a complex comprising a globally anionic biologically active substance, a cationic constituent, and an anionic constituent, by mixing anionic and cationic constituents, of which one is preferably a lipid, in a non-aqueous hydrophilic polar solvent, adding to said mixture an excess of an aqueous solution, and adding to the above mixture a globally anionic biologically active substance, such as nucleic acid, whereby a stable particular complex is formed having lamellar, rolled, and condensed structure.

Allen and Stuart, PCT/US98/12937 (WO 98/58630) disclose forming polynucleotide-cationic lipid particles in a lipid solvent suitable for solubilization of the cationic lipid, adding neutral vesicle-forming lipid to the solvent containing said particles, and evaporating the lipid solvent to form liposomes having the polynucleotide entrapped within.

Allen and Stuart, U.S. Pat. No. 6,120,798, disclose forming polynucleotide-lipid microparticles comprising dissolving a polynucleotide in a first, e.g. aqueous, solvent, dissolving a lipid in a second, e.g. organic, solvent immiscible with said first solvent, adding a third solvent to effect formation of a single phase, and further adding an amount of the first and second solvents to effect formation of two liquid phases.

Bally et al. U.S. Pat. No. 5,705,385, and Zhang et al. U.S. Pat. No. 6,110,745 disclose a method for preparing a lipid-nucleic acid particle by contacting a nucleic acid with a solution comprising a non-cationic lipid and a cationic lipid to form a lipid-nucleic acid mixture wherein the solution comprises 15-35% water and 65-85% of organic solvent; removing the aqueous portion of said mixture to form a non-aqueous lipid-nucleic acid mixture; removing the organic solvent, leaving behind a lipid-nucleic acid complex in the form of a film; and hydrating the film to form the particle.

Maurer et al., PCT/CA00/00843 (WO 01/06574) disclose a method for preparing fully lipid-encapsulated therapeutic agent particles of a charged therapeutic agent including combining preformed lipid vesicles, a charged therapeutic agent, and a destabilizing agent to form a mixture thereof in a destabilizing solvent that destabilizes, but does not disrupt, the vesicles, and subsequently removing the destabilizing agent, wherein the vesicles comprise a charged lipid having the charge opposite to that of the therapeutic agent, and wherein the vesicles contain a modified lipid having a steric barrier moiety in the amount to retard aggregation of the vesicles. The charged therapeutic agent may be anionic, for example, a nucleic acid, in which case the vesicles comprise a cationic lipid.

The above methods generally teach forming nucleic acid-lipid complexes in single phase solutions comprising organic solvents and water (aqueous-organic solutions). They do not teach the nucleic acid and lipid to be independently molecularly or micellarly soluble in said aqueous-organic solutions or the plasmid within said organic-aqueous solution to be in a condensed state.

SUMMARY OF THE INVENTION

One aspect of this invention is a process for preparing a microparticulate complex, which process comprises combining a particle-forming component and a nucleic acid-like component in a monophasic composition comprising water and a water-miscible, organic solvent to form a mixture wherein the particle forming component and the nucleic acid moiety are independently molecularly or micellarly soluble in the water/organic solvent system, and reducing the amount the organic solvent in the mixture. This effects formation of the microparticulate complex comprising the nucleic acid-like component and the particle-forming component. It is preferred that during such reducing step, the system remains monophasic, which means that its liquid components do not undergo phase separation resulting in the presence of a liquid-liquid interface, such as emulsion or liquid phase separation, but rather maintain a single liquid phase.

Another aspect of this invention is a microparticulate complex that comprises a particle-forming component complexed to a nucleic acid-like component forming an approximately spherical particle, wherein the particle-forming component encloses an interior of the particle containing the nucleic acid-like component and the so-enclosed interior volume has less than about 50% of the volume containing free water.

Another aspect of this invention is a composition comprising water and particles of a microparticulate complex, wherein the complex comprises a particle-forming component complexed to a nucleic acid-like component forming approximately spherical particles, wherein the interior volume of each microparticulate particle contains the NAC and has less than about 50% of the volume containing free water.

Still another aspect of this invention is a method for delivering a nucleic acid-like component to a cell, which method comprises contacting the cell with a composition comprising water and a microparticulate complex, which complex comprises a particle-forming component complexed to a nucleic acid-like component, forming an approximately spherical particle, wherein the enclosed interior of the particle containing the nucleic acid-based moiety has less than about 50% of the volume containing free water, and maintaining the contact for a time sufficient to allow the nucleic acid-based moiety to enter the cell.

A still further aspect of this invention is a method for delivering a therapeutic nucleic acid-like component into a patient in need thereof, which method comprises administering a composition comprising water and particles of a microparticulate complex that comprises a particle-forming component complexed to a nucleic acid-like component forming approximately spherical particles, wherein the enclosed interior of each particle contains the NAC and has less than about 50% of the volume containing free water.

Still another aspect of this invention is article of manufacture that comprises (i) a composition comprising water and particles of a microparticulate complex, wherein the complex comprises a particle-forming component complexed to a nucleic acid-like component forming approximately spherical particles, wherein the enclosed interior volume of each particle contains the NAC and has less than about 50% of the volume containing free water, and (ii) written instructions for therapeutic administration or (cell transfection).

Still another aspect of this invention is a charge-changing composition represented by the formula A-X-B. In the formula X represents a chemical bond capable of irreversible dissociation in reaction to a factor in a physiological or bioprocess environment;

A represents a molecular moiety that, upon dissociation of the bond X produces a ionically charged product; and B represents a molecular moiety, which upon the dissociation of bond X, separates from the composition leaving the remaining ionically charged product more positive than that of A-X-B itself. The composition is particularly valuable in forming the microparticulate complex of this invention.

These, and other aspects, embodiments, objects and features of the present invention, as well as the best mode of practicing the same, will be more fully appreciated when the following detailed description of the invention is read in conjunction with the accompanying drawings.

DETAILED DESCRIPTION OF THE INVENTION

Figure 1:
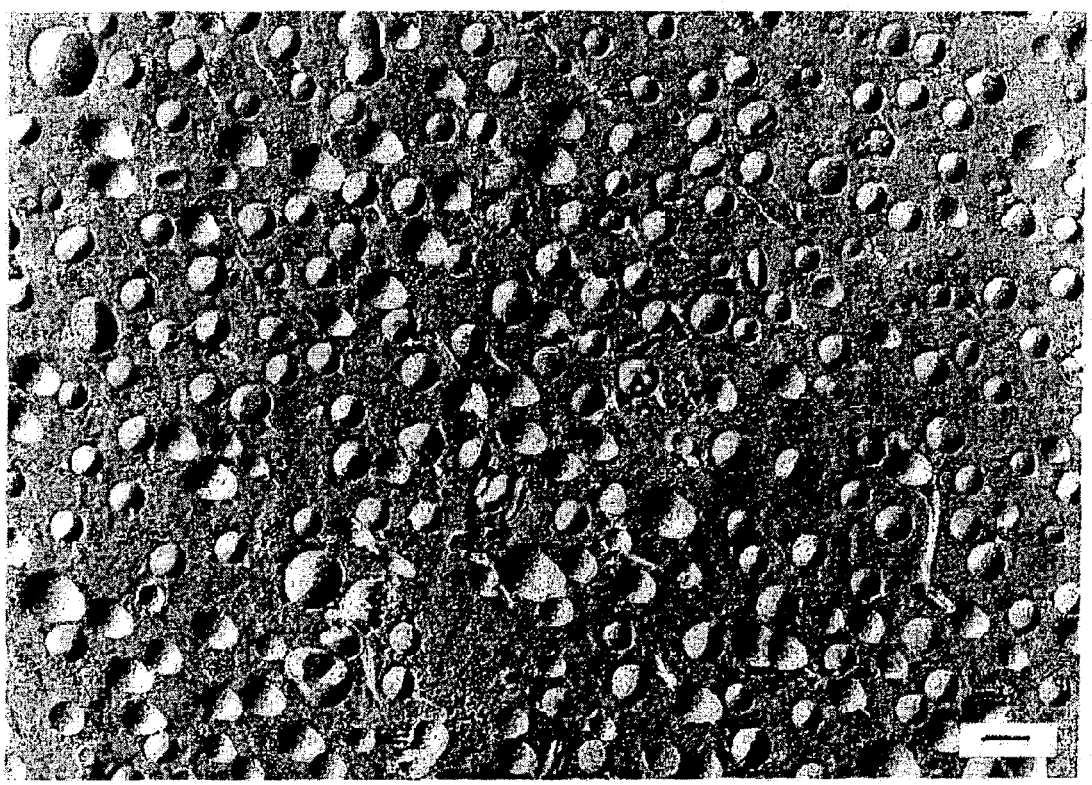
FIG. 1 represents freeze-fracture electron microscopic image of GENOSPHERES™ composed of DDAB, Cholesterol, POPC, and PEG (2,000)-DSPE (6/6/12/0.12 nmoles per micro-g of bacterial plasmid DNA). Scale bar is 100 nm.

This invention in a broad aspect relates to a new process for preparing a microparticulate complex from a particle-forming component ("PFC") and a nucleic acid-like component ("NAC"). The process has two important aspects: (1) the PFC and the NAC are contacted in a monophasic composition of water and a water-miscible solvent, and (2) the PFC and the NAC are independently molecularly or micellarly soluble in the aqueous/organic system. The PFC and the NAC are combined in the monophasic composition to form a mixture containing the microparticulate complex, and the organic solvent is then removed. The microparticulate complex is then employed to deliver the NAC to a patient, to transfect cells, or other uses consistent with this disclosure. The following discussion will further explain the detailed nature of the components employed in the process of the invention. Throughout the specification, the microparticulate complex formed by the process of this invention may also be referred to as a "GENOSPHERE" or "GENOSPHERES," a term coined specifically to refer to the composition unique to this invention.

1. The Nucleic Acid-Like Component ("NAC").

A NAC useful in the present invention is selected according to the biological or physiological effect desired to be produced, e.g. by its delivery into living cells. Such selection is well known to the skilled artisans in the fields of molecular biology and medicine (see, e.g., Gene Therapy, Ed. by D. Lasic and N. Smyth-Templeton, Marcell Dekker, N.Y., 2000, 584 pp.). The NAC is a polymeric material that is a nucleic acid or resembles in its structure and function a nucleic acid in that it exhibits a backbone of covalently linked repetitive molecular units (also referred to as monomers) and has a biological or physiological effect. The NAC may include natural, modified or synthetic bases and backbone elements. The NAC may be of natural or synthetic origin and may include a nucleic acid (i.e. a polymer that comprises a plurality of nucleic acid bases attached to a backbone of covalently linked repetitive molecular units), DNA, RNA, natural and synthetic oligonucleotides (including antisense oligonucleotides, interfering RNA and small interfering RNA), nucleoprotein, peptide, nucleic acid, ribozyme, DNA-containing nucleoprotein, such as an intact or partially deproteinated viral particles (virions), oligomeric and polymeric anionic compounds other than DNA (for example, acid polysaccharides and glycoproteins), and the like. It is preferably DNA and is more preferably DNA carrying a sequence of an expressible gene. Antisense oligonucleotides are another preferred type of nucleic acids. To signify the process of transfer of an exogenous NAC into a living cell we will use the term "transfection" without limitation to any particular kind of NAC or to any particular function that may be performed in the cell by a NAC so transferred. The transfection may be performed on cells in the body of a subject to be treated (in vivo) or on cells maintained outside a subject (in vitro or ex vivo). The terms "transfection" and "delivery" will be used interchangeably in this description of the invention. When it is advantageous for a particular application, GENOSPHERES may contain more than one kind of NAC in respect to structure, function, or nucleotide sequences.

2. The Water-Miscible Organic Solvent.

The water-miscible organic solvent maintains complete miscibility with water (single liquid phase or monophase) under the conditions chosen for the PFC/NAC combining and organic solvent amount reducing steps described below, i.e. over the entire range from about 0.01 vol. % up to about 60 vol. %.

The water-miscible organic solvent of this step is preferably an alcohol, or an aprotic solvent, and is preferably one suitable for use in biological preparation. Examples of the alcohol solvent include methanol, ethanol, 1-propanol, 2-propanol, 2-butanol, tert-butanol, ethylene glycol, diethylene glycol, propylene glycol, glycerol, methylcellosolve (ethylene glycol monomethyl ether), methylcarbitol (diethylene glycol monomethyl ether) and the like. Methanol, ethanol or tert-butanol are preferred, particularly ethanol. Aprotic solvents include an ether, an ester, a ketone, a nitrile, an amide, or a sulfoxide. The aprotic solvent is preferably ethylene glycol dimethyl ether, ethylene glycol diethyl ether, diethyleneglycol dimethyl ether, dioxane, tetrahydrofurane, acetone, methylethylketone, acetonitrile, dimethylformamide, or dimethylsulfoxide.

3. The Particle-Forming Component ("PFC").

The PFC typically comprises a lipid, such as a cationic lipid, optionally in combination with a PFC other than a cationic lipid. A cationic lipid is a lipid whose molecule is capable of electrolytic dissociation producing net positive ionic charge in the range of pH from about 3 to about 10, preferably in the physiological pH range from about 4 to about 9. Such cationic lipids encompass, for example, cationic detergents such as cationic amphiphiles having a single hydrocarbon chain. Patent and scientific literature describes numerous cationic lipids having nucleic acid transfection-enhancing properties. These transfection-enhancing cationic lipids include, for example: 1,2-dioleyloxy-3-(N,N,N-trimethylammonio)propane chloride-, DOTMA (U.S. Pat. No. 4,897,355); DOSPA (see Hawley-Nelson, et al., Focus 15(3): 73 (1993)); N,N-distearyl-N,N-dimethyl-ammonium bromide, or DDAB (U.S. Pat. No. 5,279,833); 1,2-dioleoyloxy-3-(N,N,N-trimethylammonio) propane chloride-DOTAP (Stamatatos, et al., Biochemistry 27: 3917-3925 (1988)); glycerol based lipids (see Leventis, et al., Biochem. Biophys. Acta 1023:124 (1990); arginyl-PE (U.S. Pat. No. 5,980,935); lysinyl-PE (Puyal, et al. J. Biochem. 228:697 (1995)), lipopolyamines (U.S. Pat. No. 5,171,678) and cholesterol based lipids (WO 93/05162, U.S. Pat. No. 5,283,185); CHIM (1-(3-cholesteryl)-oxycarbonyl-aminomethylimidazole); and the like. Cationic lipids for transfection are reviewed, for example, in: Behr, Bioconjugate Chemistry, 5:382-389 (1994). Preferable cationic lipids are DDAB, CHIM, or combinations thereof. Examples of cationic lipids that are cationic detergents include (C12-C18)-alkyl- and (C12-C18)-alkenyl-trimethylammonium salts, N—(C12-C18)-alkyl- and N—(C12-C18)-alkenyl-pyridinium salts, and the like.

A PFC other than a cationic lipid is typically one capable of self-assembly into monolayers and/or bilayers or the one assisting such assembly and include, for example, neutral phospholipids (e.g. phosphatidylcholine, phosphatidylethanolamine), acidic phospholipids (e.g. phosphatidylglycerol, phosphatidyl-inositol, phosphatidylserine, phosphatidic acid, cardiolipin), sphingolipids (e.g. sphingomyelin), bis-alkyl-phosphate esters (e.g. dicetylphosphate), fatty alcohols, fatty acids, fatty acid diglycerides, higher alkyl-poly(oxyethylene) ethers; higher acyl poly(oxyethylene) esters, higher alkyl polyol esters, (also termed tensides—see BACHEM Product Catalog, BACHEM California, Inc., 1999, pp. 129-130), higher acyl-polyol esters, sterols (e.g. cholesterol), derivatives thereof, or mixtures thereof.

Other PFCs include certain particle-forming polymers that are cationically charged polymers (polycations), such as: poly(ethylencimine), poly(vinylamine), poly(vinylpyridine), N-modified poly(acrylamide), and N-alkylated (e.g. quaternized) derivatives thereof; poly(amino acids)-poly(lysine), poly(arginine), poly(ornitine), and co-polymers containing them; basic proteins, such as histones, protamines, basic fibroblast growth factor, or synthetic peptides (Boulikas and Martin, Int. J. Oncology 10:317-322 (1997); Li and Huang, Gene Therapy 4:891-900 (1997); Sorgi et al. Gene therapy 4:961-968 (1997); Murphy, et al. Nucleic Acid Res. 29:3694-3704 (2001); Hoganson, et al. Human Gene Therapy 9:2565-2575 (1998)). Particle-forming polymers also may be neutral or polyanionic, or combinations thereof. Neutral particle-forming polymers include, for example, poly(lactic acid), poly(glycolic acid), a co-polymer of lactic and glycolic acid, or poly(cyanoacrylate). (Cohen, et al. Gene Therapy 7:1896-1905 (2000); Wang, et al. J. Controlled Release, 57:9-18 (1999); Lambert, et al. Int. J. Pharmaceutics 214:13-16 (2001)). While for convenience of presentation this disclosure of the invented methods and materials will refer to a PFC, it is recognized that such a reference will include a PFC alone or in combination with another PFC. Typically, if a cationic particle-forming polymer is used, the lipid would be predominantly neutral and/or anionic; if a cationic lipid is used, a particle-forming polymer would be predominantly neutral and/or anionic.

4. Combining the PFC with the NAC.

In this step a PFC is combined with a NAC under conditions that are sufficient to form the desired microparticulate complex. The selected NAC is combined with the PFC in a solution having a single liquid phase (i.e. monophasic) comprising water and water-miscible organic solvent selected as described above. The monophasic composition is a mixture characterized by the absence of liquid-liquid interfaces, without regard to its optical clarity, as discussed below. The PFC and NAC can be combined using any method known in the art. The percentage of the organic solvent by volume present in the resulting aqueous/organic solvent mixture will vary according to the type of NAC and PFC used in the process. This percentage may range from about 10% vol. to about 60% vol., generally up to about 55% volume. The temperature range at which the process takes place is above the freezing point of the aqueous/organic solvent mixture, but below the boiling point of the organic solvent; it will typically vary from about 0° C., to no more than 100° C. under ambient conditions of pressure. Temperatures above ambient, such as in the range of 30° C. to 70° C., are preferred, especially about 40° to about 65° C.

One preferred method is to prepare a solution of the NAC in an essentially aqueous medium, prepare the PFC as a solution in the organic solvent, and combine the two solutions, for example by mechanical mixing, in the volume ratio providing in the mixture the necessary content of the organic solvent. The content of the organic solvent in the resulting mixture preferably provides for partial dehydration and/or condensation of the NAC, while keeping the NAC in a dissolved state; and at the same time, the organic content solubilizes the PFC into a non-vesicular form, such as, for example, micellar form.

Another preferred method is to prepare the NAC solution in a single fluid phase containing water and a first volume percentage of the water-miscible organic solvent, prepare the PFC solution in a single fluid phase containing water and a second volume percentage of the water-miscible organic solvent, and combine these two solutions, for example by mechanical mixing, in the volume ratio providing in the mixture the necessary content of the organic solvent as specified below. The first and second volume percentages of the organic solvent in these two solutions are preferably the same. The volume percentage of the organic solvent in the first (NAC) solution is preferably chosen to facilitate the transition e.g., of the nucleic acid molecule into condensed and/or less hydrated, form, while the volume percentage of the organic solvent in the second (PFC) solution solubilizes, e.g., a lipid into a non-vesicular, such as micellar, form. Thus a skilled artisan would choose the content of the organic solvent in the nucleic acid and lipid solutions, as well as in the resulting mixture, to satisfy both the need to facilitate nucleic acid dehydration and/or condensation, and the need for lipid solubilization.

According to the third preferred method, a PFC is provided in the neat form, preferably in the form having high surface area, such as a film deposited on an insoluble substrate, and then contacted with the NAC solution in a single fluid phase containing water and water-miscible organic solvent in the volume percentage to satisfy the need for NAC dehydration/condensation and/or PFC solubilization, which percentage is more particularly defined below. Contacting of the neat PFC with the NAC solution is preferably accompanied by mechanical agitation, such as slow rotation or reciprocation of the vessel in which the contacting is conducted, so that the PFC is solubilized and contacts the NAC, preferably in a condensed state, to ensure formation of the microparticulate complex. The agitation typically continues until essentially all of the neat PFC is solubilized.

More than one particle-forming component may be used in the process of this invention. In this case, one PFC has higher affinity to the NAC than the other. For example, in using a cationic lipid with a neutral, particle-forming lipid, it may be of advantage to use the above methods in combination. Typically, the component with higher affinity, such as the cationic lipid, is combined with nucleic acid using above described two solution method, and a resulting mixture is further contacted with the second particle-forming component, such as the non-cationic, particle-forming lipid, in a neat state with slow agitation until the second component is solubilized.

In some cases it may be of advantage to introduce into the aqueous solution of the NAC an amount of nucleic acid-condensing compound sufficient to promote further condensation of the NAC, e.g., into a tight globular form, which is discussed in greater detail herein. Such nucleic acid-condensing compounds are known in the art. Examples include polyamines (spermine, spermidine), and cationic dyes (e.g. acridine derivatives).

The organic solvent in the resulting NAC/PFC solution is preferably present at the volume concentration at which both the NAC, such as nucleic acid, and the PFC, such as lipid, are independently molecularly or micellarly soluble. That is, the organic-aqueous monophase produced after combining the NAC with the PFC would be able to dissolve either the NAC or the PFC in the form of a molecular or micellar solution without the need of both NAC and PFC to be present during the dissolution. Preferably, when the content of the organic solvent, and/or the temperature at which NAC and PFC are combined, is decreased, PFC forms a self-assembled, non-micellar, condensed phase, such as bilayer, inverted hexagonal, cubic, liquid crystalline, or amorphous phase. PFC that in aqueous environment form ordered condensed phases, such as bilayers, cubic, or inverted hexagonal phases, known as lyotropic liquid crystals, are particularly preferred. Such PFC are known (see, for example, D. Lasic, Liposomes: From Physics to Applications, 1993). Bilayer-forming PFC in aqueous environment typically form enclosed structures, such as vesicles. Preferentially, the ability of PFC to form a self-assembled, condensed phase upon reduction of the organic solvent concentration in the monophase is independent of whether or not a NAC is present. Exemplary classes of PFC that form self-assembled, non-micellar, condensed phases in aqueous environment are described in: Donald M. Small, Handbook of Lipid Research, Volume 4, The Physical Chemistry of Lipids: From Alkanes to Phospholipids, Plenum Press, 1986, Chapter 4, the teachings of which are incorporated herein by reference. These exemplary NAC are designated as Class I insoluble, non-swelling amphiphiles (spread on interface to form stable monolayer: water-insoluble or having very low solubility) and Class II—insoluble, swelling amphiphiles (spread to form stable monolayer at interface and are insoluble but swell in water to form lyotropic liquid crystals). Particular examples of such PFC are disclosed in Section 3 herein. While Small, supra, teaches the amphipiles to be lipids, it is recognized that the same physico-chemical characteristics of condensed, ordered phases may be achieved using PFC comprising polymers. Without being limited by a theory, we believe that when so chosen, the organic solvent concentration in the monophase facilitates the rearrangement of PFC molecules around the nucleic acid molecules to form the microparticulate complex with advantageous properties for transfecting cells.

Lipids are generally known to form micellar solutions in water in the presence of sufficiently high concentration of solubilizing detergents such as for example, octylglucoside, cholate (anion of cholic acid), and deoxycholate (anion of deoxycholic acid). The art discloses the use of detergents as lipid-solubilizing aids to form nucleic acid-lipid complexes in aqueous solutions of nucleic acids wherein the detergents are eventually removed to effect particle-formation (see e.g., Wheeler et al., U.S. Pat. No. 5,976,567). The instant invention, however, greatly reduces or eliminates altogether the requirement for solubilizing detergents to provide for micellar or molecular solution of the lipids in the selected organic-aqueous monophase, although molecules with detergent properties may be used as components of GENOSPHERE particles.

The particular concentration of the organic solvent selected for any given mixture would depend on the nature of the organic solvent, the PFC, and the NAC; the temperature at which the components are combined; the ionic strength of the aqueous component; and the concentration of PFC and/or NAC in the mixture. Once the organic solvent, the NAC, the aqueous component, and the PFC are selected according to the needs of a particular application of this invention, a skilled artisan being guided by this specification, would easily establish the required concentration of the organic solvent by performing simple solubility tests known in the art. For example, to perform the solubility test, the NAC and the PFC can be independently admixed (in separate containers) into the organic-aqueous monophase having several concentrations of the organic solvent at the chosen temperature, and the molecular or micellar nature of the dissolved nucleic acid and/or lipid can be determined by dynamic light scattering wherein the molecular or micellar character of dissolution is indicated, in the case of PFC, by predominance of particles having the size of less than about 30 nanometers (nm), typically 20 nm or less, while in the case of the NAC, the conformity of the dissolved particles to the calculated size of a compact globule for a given NAC would indicate that they are molecularly dissolved. Light scattering intensity can be used as well, since micellar or especially molecular (true) solutions have substantially lower light scattering than those containing particles, vesicles, filaments, or other elements comprising aggregated NAC or PFC phases. Other methods know in the art, such as NMR, ESR probe, and fluorescent probe methods can be used to detect the presence of NAC or PFC in the state other than micellar or molecular solution. See, for example, R. Haugland, 1996, Handbook of Fluorescent Probes, Molecular Probes, Inc., Oregon, USA.

The amount of an organic solvent in the mixture is so elected as to provide for NAC and PFC to be independently micellarly or molecularly soluble in the resulting aqueous-organic solvent monophase. Typically this amount is from about 10 vol. % to about 60 vol. %, preferably from 30 vol. % to 55 vol. %, and most preferably from about 45 vol. % to about 55 vol. %. When the PFC is a lipid and the NAC is a nucleic acid, the lipid typically comprises a cationic lipid in the amount equivalent from about 0.2 to about 3.0 molecules per nucleic acid base, more preferably from about 0.5 to about 2.0 molecules per nucleic acid base. The amount of a non-cationic lipid is preferably such as to promote the lipid bilayer formation upon reduction of the organic solvent content in the mixture, as described below. Any particular amount of non-cationic lipids will depend on the nature of this lipid, the chosen cationic lipid, the nucleic acid, and the organic solvent. Typically, non-cationic lipids may be present in the molar ratio of 0.2 to 10.0, preferably from 0.5 to 5.0, to the amount of the cationic lipid. Sterols may be present in the amount of up to 100% of the non-cationic lipid. If phospholipids, such as for example, phosphatidylcholine, are present, sterols, such as for example, cholesterol, typically will constitute up to 50 mol. % of the non-cationic lipid. The nucleic acid solution and the lipid, whether in solution or in a neat form, are preferably combined at the temperature above ambient and above the highest of the phase transition temperatures of the lipids present in the solution, but below the boiling point of the organic solvent, more preferably between about 30° C. and about 80° C., yet more preferably between about 40° C. and about 70° C., and optimally between about 50° C. and 65° C. The precise temperature at which the NAC and PFC are combined also provides for molecular or micellar dissolution of both components in the chosen monophase. This temperature can be determined, for example, by the solubility tests described above.

Aqueous component of the fluid phase is preferably of low ionic strength, i.e. at or below the physiological value (that of 144 mM NaCl), more preferably below that of 50 mM NaCl, and most preferably less than that of 10 mM NaCl. Ionic strength is defined as one-half the sum of concentrations of all ions in a solution multiplied by the square of their ionic charges (see Cantor and Schimmal, Biophysical Chemistry, Part 2, Freeman, N.Y. 1980, p. 677). Without being limited by a particular theory, we believe that low ionic strength at the PFC/NAC combining step reduces the risk of particle aggregation and precipitation and eliminates the requirement of sterically stabilizing lipid components to be present during this step. The aqueous component may also contain buffer substances to maintain the desired pH, typically in the range from about 3.0 to about 10.0, more preferably in the physiological pH from about 4.0 to about 9.0. The amount of the buffer substance is chosen to keep the ionic strength low, within the above range of ionic strength.

5. Reducing the Amount of the Organic Solvent in the Mixture.

After combining the NAC and PFC in accordance with the foregoing discussion, the amount of the organic solvent in the mixture is reduced to effect formation of GENOSPHERES. It is believed that in the case of PFC comprising a lipid, reduction of the organic solvent contents promotes lipid bilayer formation around the condensed NAC/PFC core, this effecting the formation and stabilization of GENOSPHERES. Thus, the amount of organic solvent is preferentially reduced to the point of self-assembly of the NAC-PFC complex into particles. If, as evidenced, for example, by particle size measurements, the formation of NAC-PFC particles occurs at the monophase step, removal of organic solvent is optional, and may serve the purpose of, for example, improving biocompatibility of the transfecting formulation. If PFC contains lipids, the amount of organic solvent is preferably reduced to, or below, the point where bilayer formation is achieved. Generally, this amount is less than about 20 vol. %. Most preferably, essentially all of the organic solvent is removed, e.g. down to about 0.01 vol. %; however in some topical applications, such as the nucleic acid delivery to the cells of skin, it is advantageous to a pharmaceutically acceptable organic solvent and retain a percentage of the solvent (e.g. ethanol) in the composition. Reduction of the organic solvent is achieved by any means available in the art, such as, for example, by dialysis, gel-chromatography, absorption, evaporation under reduced pressure, ultrafiltration, size-exclusion chromatography, lyophilization, or a combination thereof. It also enables the GENOSPHERES to be transferred into appropriate medium for storage or final use. Prior to, or in the course of, the reduction of the organic solvent content in the mixture, the ionic strength of the medium can be brought up to physiological value (that of 144 mM NaCl), for example, by addition of the concentrated salt solution, followed by mixing. It was unexpectedly found that the GENOSPHERES of this invention remain stable against aggregation in physiological salt solutions even in the absence of aggregation-preventing polymer-lipid conjugates.

In some organic-aqueous systems taught by the art liquid-liquid interfaces may be present even if the system appears optically clear (a "clear single phase") such as in a microemulsion. In the present invention, a monophasic (single liquid phase) organic-aqueous composition is characterized by the absence of liquid-liquid interfaces, without regard to its optical clarity. The monophase form of the mixture is maintained while the content of the organic solvent in the mixture is reduced, avoiding the formation of more than one liquid phase. Formation of more than one liquid phase is manifested by the emergence of liquid/liquid interfaces, often leading to the formation of a (micro)emulsion, or to separation of the second liquid phase. It is believed that avoiding the formation of a second liquid phase prevents PFC from being transferred to the liquid/liquid interface and/or extracted into organic-rich second phase, both phenomena being adverse for the correct assembly of NAC/PFC microparticles. Formation of a second liquid phase may be promoted by halogenated hydrocarbons, e.g. chloroform, having incomplete miscibility with aqueous fluids.

The temperature at which the organic solvent is removed is preferably the one at which the NAC was combined with the PFC. However the temperature can be first brought to ambient or below up to refrigeration temperature of 4-8° C. The latter is more suitable when low phase transition temperature (Tm) lipids, such as the ones containing unsaturated fatty acid chains (Tm<4° C.), are used.

In addition, cell-specific ligands and auxiliary components (described in Section 7, below) can be added to GENOSPHERES during the contact step discussed above prior to formation of GENOSPHERES or after the formation of the GENOSPHERES. GENOSPHERES can be optionally purified from any lipid aggregates lacking the NAC, e.g. by density gradient centrifugation. Finally, GENOSPHERES can be transferred into a suitable medium or lyophilized for storage as described below and further reconstituted in a biologically acceptable medium (e.g. water, physiological aqueous solutions, or other injectable vehicles) for final use. The agents aiding the biodistribution and tissue penetration can be added to a GENOSPHERE formulation. These include mannitol or vasoactive substances (see e.g., Rosenecher et al., Proc. Natl. Acad. Sci. USA, 1996, vol. 93, pp. 7236-7241).

6. Structural and Physical Properties of the Microparticulate Complex

The size of the GENOSPHERE formed in accordance with this invention is within the range of about 40 to 1500 nm, preferably in the range of about 50-500, an most preferably, in the range of about 20-50 nm. In another embodiment, the size the GENOSPHERE ranges from about 60 nm to about 350 nm. This size selection advantageously aids the GENOSPHERE, when it is administered to the body, to penetrate from the blood vessel into the diseased tissues such as malignant tumors, and transfer a therapeutic nucleic acid therein. It is also a characteristic and advantageous property of the GENOSPHERE that its size, as measured for example, by dynamic light scattering method, does not substantially increase in the presence of extracellular biological fluids such as in vitro cell culture media or blood plasma.

Electron microscopic analysis is useful for determining the structure of a GENOSPHERE. Such an analysis of a GENOSPHERE particle reveals a NAC-containing core and a shell surrounding the core, as shown on FIG. 1 and FIG. 2. The core appears homogenous on the freeze-fracture electron microscopy preparations. The shell exhibits the structural behavior characteristic for a bilayer of a vesicle-forming lipid as it produces a smooth fracture plane using on the freeze-fracture electron microscopy preparations. Thus, the vesicle-forming PFC, e.g. a lipid of the shell is preferably self-organized in one or more bilayers surrounding the core. For example, the cationic lipid content of the shell, if any, is low enough so that when the GENOSPHERE is reacted with a strong polyanion, such as heparin, polyphosphate, or chondroitin sulfate, the dissociation of the GENOSPHERE is minimal, and liberation of a nucleic acid from the GENOSPHERE is less than 30%, typically less than 10% of the total nucleic acid content of the GENOSPHERE. An advantageous feature of GENOSPHERES is that the PFC, e.g. cationic lipid content, while being high in the GENOSPHERE overall, is lower in the GENOSPHERE shell. Low cationic lipid content in the GENOSPHERE shell prevents the GENOSPHERE from dissociation by the polyanionic substances surrounding the cell e.g. within the body, reduces GENOSPHERE aggregation in the blood and "opsonization" by blood proteins which is known to cause rapid elimination of the nucleic acid-carrying particles from the body. Therefore more of the nucleic acid can reach target cells. At the same time, the high overall content of cationic lipids in the particle enhances the nucleic acid delivery.

The shell surrounds the core closely so that between the core and the shell there is little space holding extraneous small molecules (solutes). Typically, the aqueous content of the inner space enclosed by the shell is less than 50%, and more preferably, 20% or less of that calculated from the particle size. The latter value corresponds to the expected amount of water immobilized in the hydration layer of the nucleic acid contained within the particle. Thus, GENOSPHERES in an aqueous medium typically would contain encapsulated water in the amount approximating the hydration water immobilized by the encapsulated nucleic acid.

Another unexpected physical property of GENOSPHERES containing lipid PFC is the uniformity of their buoyant density which typically falls within the range of 1.025-1.06 g/cm$^3$. Upon centrifugation in the sucrose density gradient, GENOSPHERES prepared under various conditions showed single sharp band corresponding to the buoyant density in the region of 1.025-1.055 g/mL, whereas the nucleic acid-lipid particles taught by the art typically have a broad distribution of buoyant densities that manifests non-uniformity of the lipid content among the particles and necessitates further purification by differential centrifugation (U.S. Pat. No. 5,972,600; Xu, et al. Biophys. J. 77:341-353 (1999)). On the contrary, the uniform buoyant density of GENOSPHERES manifests the uniformity of lipid and nucleic acid content among particles that gives then the advantage of better manufacturing control and standardization.

7. Association with Cell-Targeting Ligands

A GENOSPHERE made in accordance with this invention also optionally contains associated therewith a ligand that facilitates the GENOSPHERE's entry into a cell, i.e. a cell-specific ligand. The ligand is a chemical moiety, such as a molecule, a functional group, or fragment thereof, which is specifically reactive with the cell of choice while being less reactive with other cells thus giving GENOSPHERE an advantage of transferring NACs, e.g. nucleic acids, selectively into the cells of choice. By being "reactive" it is meant having binding affinity to a cell or tissue, or being capable of internalizing into a cell wherein binding affinity is detectable by any means known in the art, for example, by any standard in vitro assay such as ELISA, flow cytometry, immunocytochemistry, surface plasmon resonance, etc. Usually a ligand binds to a particular molecular moiety—an epitope, such as a molecule, a functional group, or a molecular complex associated with a cell or tissue, forming a binding pair of two members. It is recognized that in a binding pair, any member may be a ligand, while the other being an epitope. Such binding pairs are known in the art. Exemplary binding pairs are antibody-antigen, hormone-receptor, enzyme-substrate, nutrient (e.g. vitamin)-transport protein, growth factor-growth factor receptor, carbohydrate-lectin, and two polynucleotides having complementary sequences. Fragments of the ligands are to be considered a ligand and may be used for the present invention so long as the fragment retains the ability to bind to the appropriate cell surface epitope. Preferably, the ligands are proteins and peptides comprising antigen-binding sequences of an immunoglobulin. More preferably, the ligands are antigen-binding antibody fragments lacking Fc sequences. Such preferred ligands are Fab fragments of an immunoglobulin, F(ab)$_2$ fragments of immunoglobulin, Fv antibody fragments, or single-chain Fv antibody fragments. These fragments can be enzymatically derived or produced recombinantly. In their functional aspect, the ligands are preferably internalizable ligands, i.e. the ligands that are internalized by the cell of choice for example, by the process of endocytosis. Likewise, ligands with substitutions or other alterations, but which retain the epitope binding ability, may be used. The ligands are advantageously selected to recognize pathological cells, for example, malignant cells or infectious agents. Ligands that bind to cell surface epitopes are preferred. One especially preferred group of ligands are those that form a binding pair with the tyrosine kinase growth factor receptors which are overexpressed on the cell surfaces in many tumors. Exemplary tyrosine kinase growth factors are VEGF receptor, FGF receptor, PDGF receptor, IGF receptor, EGF receptor, TGF-alpha receptor, TGF-beta receptor, HB-EGF receptor, ErbB2 receptor, ErbB3 receptor, and ErbB4 receptor. EGF receptor vIII and ErbB2 (HEr2) receptors are especially preferred in the context of cancer treatment using GENOSPHERES as these receptors are more specific to malignant cells, while scarce on normal ones. Alternatively, the ligands are selected to recognize the cells in need of genetic correction, or genetic alteration by introduction of a beneficial gene, such as: liver cells, epithelial cells, endocrine cells in genetically deficient organisms, in vitro embryonic cells, germ cells, stem cells, reproductive cells, hybrid cells, plant cells, or any cells used in an industrial process.

The ligand may be attached to the GENOSPHERE by any suitable method available in the art. The attachment may be covalent or non-covalent, such as by adsorption or complex formation. The attachment preferably involves a lipophilic molecular moiety capable of conjugating to the ligand by forming a covalent or non-covalent bond, and referred to as an "anchor". An anchor has affinity to lipophilic environments such as lipid micelles, bilayers, and other condensed phases, and thereby attaches the ligand to a lipid-nucleic acid microparticle. Methods of the ligand attachment via a lipophilic anchor are known in the art. (see, for example, F. Schuber, "Chemistry of ligand-coupling to liposomes", in: Liposomes as Tools for Basic Research and Industry, ed. by J. R. Philippot and F. Schuber, CRC Press, Boca Raton, 1995, p. 21-37). Typically, an amount of a lipophilic anchor effective to provide ligand conjugation is included into the PFC, e.g. lipid, prior to, or during, the GENOSPHERE formation. Alternatively, the conjugate of an anchor and a ligand can be first formed, and then incorporated into GENOSPHERES by addition to the lipid prior to the GENOSPHERE formation, or by addition of the conjugate to the aqueous suspension of GENOSPHERES after their formation. A particularly suitable mode of ligand attachment to GENOSPHERES is by using a ligand conjugated to a lipophilic anchor through an intermediate hydrophilic polymer linker. Thus, the ligand moves freely above the GENOSPHERE surface and can react even with hard-to-reach epitopes on the cell surface. Ligands conjugated to lipophilic anchors via a hydrophilic polymer intermediate linker advantageously become stably associated with preformed nucleic acid-lipid GENOSPHERES of the present invention during co-incubation of the conjugated ligands and the GENOSPHERES in an aqueous medium. (U.S. Pat. No. 6,210,707).

8. Transfection Enhancing Components.

GENOSPHERES can further comprise other components beneficial for its function of transfecting cells. These can be viewed as transfection-enhancing components, i.e. an entity associated with the GENOSPHERE that improves the delivery of an exogenous NAC to a living cell. These beneficial, transfection-enhancing components, may include, without limitation, endosome-escape agents (see, e.g., Drummond et al., Progress in Lipid Research, 2000, vol. 39, p. 409-60; Kichler et al., Bioconjugate Chem., 1997, vol. 8 p. 213-221; Lee and Huang, J. Biol. Chem., 1996, vol. 271, p. 8481-8487), nuclear localization factors (see, e.g., Antopolsky et al., Bioconjugate Chem., 1999, vol. 10, p. 598-606; Branden et al., Nature Biotechnology, 1999, vol. 17, p. 784-787; Pouton, Adv. Drug. Del. Rev., 1998, vol. 34, p. 51-64; Sebestyen et al., Nature Biotechnology, 1998, vol. 16, p. 80-85; Zanta et al., Proc. Natl. Acad. Sci. USA, 1999, vol. 96, p. 91-96), triggerable means for enhanced transfer into cytosol (see, e.g., Reddy and Low, J. Controlled Release, 2000, vol. 64 p. 27-37; Drummond and Daleke, Chem. Phys. Lipids 1995, vol. 75, p. 27-41; Kirpotin et al., FEBS Lett., 1996, vol. 388, p. 115-118; Thompson et al., Biochim. Biophys. Acta, 1996, vol. 1279, p. 25-34; Rui et al., J. Am. Chem. Soc., 1998, v. 120, p. 11213-11218), pH-sensitive compounds (see, e.g., Lee and Huang, J. Biol. Chem. 1996, vol. 271, p. 8481-8487; Leroux et al., J. Controlled Release, 2001. vol. 72 p. 71-84), heat and radiation-triggerable release (e.g., Gaber et al., Pharm. Res., 1995, vol 12, p. 1407-16; Gaber et al., Int. J. Radiat. Oncol. Biol. Phys., 1996, vol. 36, p. 1177-1187; Kong et al., Cancer Res., 2000, vol. 60, p. 6956-6957; Needham and Dewhirst, Adv. Drug Delivery. Rev., 2001, vol. 53, p. 285-305; Yatvin et al., Science 1978, vol. 202, p. 1290-3; Saalman et al, Biochim. Biophys. Acta, 1991, vol. 1064, p. 124-130) and membrane fusion promoters such as membrane fusion-enhancing or membrane fusion-inducing compounds (see, e.g., Glushakova et al., Biochim. Biophys. Acta, 1992, vol. 1110, p. 202-208; Kichler et al., Bioconjugate. Chem. 1997, vol. 8, p. 213-221; Simoes et al., Gene Therapy, 1999, vol. 6, p. 1798-1807; Wagner, Adv. Drug Delivery Rev., 1999, vol. 38, p. 279-289), intracellular nucleic acid release-enhancing or inducing components, transcription factors, and promoter-modulating compounds (see, e.g., Kaiser and Toborek, J. Vascular Res., 2001, vol. 38 p. 133-43; Jain and Gewirtz, J. Mol. Medicine, 1998, vol. 76, p. 709-714). Examples and modes of use of such beneficial components are described in the above cited scientific publications and are known in the art of gene and nucleic acid delivery to cells.

9. Surface Modification Using Hydrophilic Polymers.

GENOSPHERES also optionally contain an amphiphilic lipid in the amount effective to further stabilize GENOSPHERES against aggregation. The amphiphilic lipid is preferably a hydrophilic polymer-lipid conjugate, more preferably a poly(ethylene glycol)-lipid conjugate. The poly (ethylene glycol)-lipid conjugate is preferably a poly(ehylene glycol) conjugate of a phospholipid, a sphingolipid, a diacylglycerol, or a sterol. The poly(ethylene glycol) portion of the conjugate has molecular weight of 250-20,000, preferably 500-10,000, more preferably 1,000-5,000. The aggregation-preventive amount of the amphiphilic lipid is less than 5 mol. %, typically less than 1 mol. % of the PFC content of the GENOSPHERE, and preferably between 0.05 mol. % and 0.5 mol. % of the lipid content of the GENOSPHERE. Also effective amphiphilic lipids are polyoxyethylene ethers of fatty alcohols, or polyoxyethylene esters of fatty acids, in the amount of less than 10 mol. %, typically, less than 5 mol. % of the total lipid. Examples of such fatty alcohol/fatty acid polyoxyethylene compounds are tenzides and those known by their trade names TWEEN 20 (polyoxyethylenesorbitan monolaurate), TWEEN 80 (polyoxyethylenesorbitan monooleate), TWEEN 60 (polyoxyethylenesorbitan monostearate), and BRIJ-35 (polyoxyethylene (23) monolauryl ether). Amphiphilic lipids are added to the lipid solution or to the nucleic acid-like component solution before combining them; alternatively, in a preferred way, amphiphilic lipids can be added to the preformed GENOSPHERES before or after removal of the organic solvent from the organic-aqueous monophase containing NAC and PFC, and incubated for the time sufficient for such lipids to "anchor" onto or combine with the surface lipid layer of the GENOSPHERES. Surprisingly, the addition of amphiphilic lipids in the amounts as low as 0.25 mol. %, dramatically improved the passage of GENOSPHERES through sterilizing filters, which provides great advantage in the industrial scale-up and production of pharmaceuticals using GENOSPHERES.

If the need arises to improve pharmacokinetic properties of the GENOSPHERES, such as to prolong their blood circulation times, amphiphilic lipid may be included in the composition of the GENOSPHERE for this purpose. In this case, the amount of amphiphilic lipid, preferably a hydrophilic polymer-lipid conjugate, such as poly(ethylene glycol)-lipid, would be more than 1 mol. % of total PFC, more preferably between 1 mol % and 20 mol % of total PFC, and optimally between 3 mol. % and 10 mol. % of the GENOSPHERE's total PFC. If the amount of surface-attached polymer on the GENOSPHERE interferes with transfection activity, the use of polymer-lipid conjugates with releasable polymer moieties (Zalipsky and Gabizon, U.S. Pat. No. 6,365,179; Zalipsky, U.S. Pat. No. 6,342,244) or those that can dissociate from the GENOSPHERE in vivo (Semple, et al. U.S. Pat. No. 6,287,591; Holland, et al. U.S. Pat. No. 5,885,613) can be used. Amphiphilic, circulation-prolonging lipid may be an oligo (oxyalkylene) lipid derivative such as for example, an oligo (ethylene glycol) derivative of a phospholipid, sphingolipid, cholesterol, or diacylglycerol, having oligo(ethylene glycol) portion with molecular weight of less than 500. In this case, in order to achieve longer circulation times, the molar proportion of such lipid may be more than 20 mol. % based on the total lipid content. Circulation-extending properties of amphiphilic polymer-lipid conjugates are known in the art. Another examples of circulation-prolonging lipids are oligoglycerol lipid derivatives, phosphatidyl glycerols, glycophospholipids, and phosphatidylinositols.

10. Using Charge-Changing Lipids.

Cationic particle-forming components such as cationic lipids and polymers advantageously form transfection-active complexes with nucleic acids. However the pharmacokinetic properties of such complexes are often poor because of the cationic charge at near-neutral pH typical for blood or plasma, therefore effectiveness of these complexes upon systemic administration to a subject is reduced. One method to overcome this disadvantage is to include into the GENOSPHEREs charge-changing particle-forming components, such as charge-changing lipids. Charge-changing lipids are ionizable lipids whose ionic charge changes with the change in their molecular environment.

One known type of charge-changing lipids are titratable lipids. Titratable lipids change the value of their ionic charge with the changes of pH in the range of 3-10, typically in the physiological range of 4-9. Titratable lipids may be cationic or anionic. Cationic titratable lipids increase their positive charge at lower pH, and reduce it at neutral or higher pH. Examples of cationic titratable lipids are primary, secondary, or tertiary lipophilic amines (1,2-Dioleoyloxy-3-N,N-dimethylaminopropane (DODAP), 1,2-dimyristoyloxy-3-N,N-dimethylaminopropane (DMDAP), 1,2-distearoyloxy-3-N,N-dimethylaminopropane (DSDAP), stearylamine, dimethylaminopropylcarbamoyl-cholesterol (DC-Chol) and lipophilic imidazole derivatives (Solodin et al. Biochemistry, 34:13537-13544 (1995)). Anionic titratable lipids reduce their negative charge at lower pH, and increase it at neutral or higher pH. Examples of anionic titratable lipids are fatty acids, diacid diacylglycerol esters (3-succinyl-1,2-($C_{12}$-$C_{18}$)-diacyl-glycerol, 3-glutaryl-1,2-(C12-C18)-diacylglycerol), diacid cholesteryl esters (cholesteryl hemisuccinate), N-glutaryl-phosphatidylethanolamine, N-succinyl-phosphatidylethanolamine, and amphiphilic (thio)lactones (N—(C12-C18)-acyl-homocysteine thiolactone). Particularly useful anionic titratable lipids are 1,2-dioleoylglyceryl-3-hemisuccinate (DOGHEMS) and cholesteryl-3-hemisuccinate (CHEMS), as well as their glutaryl analogs. When in blood circulation (pH 7.2-7.4), the ionic charge of the GENOSPHERES containing such lipids is neutral or negative, favorable for higher persistence in the blood and distribution into the diseased tissues, such as tumors; when engulfed by the cells, because of the acidified environment of cellular endosomes (pH 5.0-6.5) the charge becomes more positive favoring nucleic acid entry into cell cytoplasm. Cationic titratable lipids can constitute up to 100 mol. %, preferably no more than 50 mol. %, of the total cationic lipid of the GENOSPHERES. Anionic titratable lipids would be present in the molar amount less than that of the cationic polymer or lipid, and preferably in the amount equal or more than one required to neutralize the cationic lipid charges in excess to nucleic acid ionic charge. It was found that a combination of a non-titratable cationic lipid and a titratable anionic lipid in a PFC of GENOSPHERES is equally effective in imparting charge-changing properties as the use of a titratable cationic lipid.

11. Using "Caged" Charge-Changing Lipids and Polymers.

While using titratable cationic and/or anionic lipids is sometimes advantageous in the compositions of this invention, the use is limited by the reversible character of the changes in their ionic charges in response to the changes of their molecular environment, and by the fact that the use of factors other than pH in the charge-changing process is not possible. Therefore according to the present invention, a class of amphiphilic compounds, e.g. lipids and polymers, is introduced that has the property of irreversibly producing a cationic charge from a neutral one, or a neutral charge from an anionic one, or a cationic charge from an anionic one, in response to the factors present within, or around, the cells to be transfected. These invented compounds will be referred to as "caged" charge-changing compounds. The "irreversible" character of the charge change means that once the charge change occurred in response to a factor, the original charge will not be restored when such factor is removed. For example, a titratable cationic lipid or polymer will revert from its cationic form to its uncharged form when the charge-changing factor, such as acidic pH, is reversed back to neutral; not so the "caged" cationic lipid sensitive to low pH according to the present invention. These "caged" charge-changing compounds, especially suited in use for nucleic acid delivery systems, such as GENOSPHERES, but also useful in other drug delivery systems and various bio/technological applications, have a general structure of:

A-X-B wherein X is the chemical bond capable of irreversible dissociation in the desired physiological or bioprocess environment, such as for example, existing in or around the cells to be transfected (a "dissociating" bond); A is a molecular moiety that upon dissociation of said bond X produces a charged product that remains associated within said drug delivery system and has ionic charge; and B is a molecular moiety which upon dissociation of X dissociates from said drug delivery system, and wherein the ionic charge of said remaining product is more positive than that of the A-X-B compound itself.

Within a drug delivery system, X would dissociate in response to the change in the physiological environment in which the permanent change in the ionic charge of the drug delivery system is desirable, or upon an exogenous stimulus designed to change the ionic charge of the drug delivery system. Examples of such physiological environment changes are changes in pH e.g. acidification, such as the acidification of an endosomal vesicle in the cell, or the action of an enzyme, a metabolite, an exogenous compound, or of an endogenous or exogenous physical factor (heat, ionizing radiation, light) that acts as a catalyst or a reactant to effect dissociation of the bond X. The enzyme may be for example, a hydrolase (an esterase, a phosphatase, a peptidase), a liase, an oxidase or a reductase present in or around the cells or tissues whereto the drug is to be delivered, or in the context of nucleic acid delivery, in or around the cells to be transfected with the nucleic acid.

X preferentially dissociates by the chemical processes of hydrolysis, elimination, oxidation, or reduction. Hydrolysis and elimination are preferred. Examples of preferred types of such dissociating bonds are:

| Bond | Dissociating factor: |
| --- | --- |
| Hydrazone, oxime, enamine | Acid catalyzed elimination (pH 2–6), exchange with endogenous carbonyl compounds (pyruvic acid) |
| 1,3-oxazolidine, ketal, acetal | Acid-catalyzed hydrolysis (pH 2–6) |
| Ortho ester of carbonic acid | Acid-catalyzed hydrolysis (pH 2–6) |
| Vinyl ether | Acid-catalyzed hydrolysis (pH 2–6) |
| Monoester or monoamide of maleic acid, citraconic acid, and of other 3,4-substituted maleic acids | Acid-catalyzed hydrolysis (pH 2–6) |
| Carboxylic acid ester | Base-catalyzed hydrolysis (pH > 7.5), enzymatic hydrolysis (esterases, lipases) |
| Phosphoric acid ester | Base-catalyzed hydrolysis, enzymatic hydrolysis (phosphatases) |
| Peptide | Enzymatic hydrolysis (peptidases, proteases) |
| Ether (carbohydrate) | Enzymatic hydrolysis (glycosidases, polysaccharide hydrolases) |
| alpha-Carboxy-2-nitrobenzyl derivatives | Light (<360 nm), radiation |
| 1-(2-nitrophenylethyl) derivatives | Light (<360 nm), radiation |
| 4,5-dimethoxy-2-nitrobenzyl (DMNB) and 4,5-dimethoxy-2-nitrobenzyloxycarbonyl (NVOC) derivatives | Light (340–360 nm), radiation |
| Desoxybenzoinyl derivatives | Light (360 nm), radiation |
| 5-Carboxymethoxy-2 nitrobenzyl (CMNB) derivatives | Light (320 nm), radiation |
| Bis-azocarboxylic acid derivatives | Heat, free radicals |

Dissociating bond X may be covalent or noncolvalent. An example of non-covalent dissociable bond X is a metal ion chelate, such as nitrilotriacetate-nickel (II)-oligo(histidine) known in the affinity chromatography for purification of recombinant proteins. Another example of a metal ion chelate bond is a bis-ammino-bis-carboxylic acid complex of a transition metal (II) such as platinum. Such bonds will dissociate by exchange reaction with the strong chelator such as EDTA or DTPA, typically at concentration 1 mM or less. Another example of dissociating non-covalent bond is oxazole-hydroxyphenylhydroxamate complex which dissociates in response to pH changes.

In the context of nucleic acid delivery, A is typically a cationic lipid or a cationic polymer having additional functionality to accommodate bond X. Cationic lipids known in the art can be used as a basis for A. Especially suitable are cationic lipids that have more than one cationic group, of which only one is reactive to form an A-X-B construct. This molecule while relatively stable in aqueous medium at neutral or slightly alkaline pH (pH>7.0), when endocytosed by a cell, will be quickly hydrolyzed in the acidic environment of the endosome and regenerate the original cationic lipid having two positively charged ionic groups. B is typically a functional group producing a hydrophilic dissociation product and preferably has an anionic charge. Thus, prior to dissociation of the bond X, the overall cationic charge of A in A-X-B is reduced or replaced by the anionic charge of B. After dissociation of the bond X, B leaves, taking away its anionic charge, and thus increasing the cationic charge of the remaining product A. For example, in a cationic lipid having one amino group and one quaternary ammonium group, the amino group is conveniently modified with citraconic acid anhydride (2-methylmaleic acid anhydride) to form a "caged" cationic lipid having overall neutral charge due to the presence of a second carboxylic group in the citraconic acid molecule. Alternatively, B does not have an ionic charge but when released through dissociation of the bond X, leaves behind a cationic group, such as an amine group. Therefore it is understood that increasing the cationic charge of A as a result of dissociation of the bond X includes situations where no cationic charge preexisted in A-X-B. To ensure the irreversible character of the dissociation, B optionally comprises a self-immolating functional group, that is, the functional group that disintegrates into smaller fragments after dissociation thus further Self-immolating chemical groups are known in the art. Examples of such groups are light-sensitive CMNB and NVOC groups (above), and hydrolysis-sensitive acetoxymethyl ester group.

Following are the exemplary constructs A-X-B that form cationic lipids or nucleic acid-binding cationic polymers upon dissociation of X ("caged" cationic lipids):

"Caged" cationic lipid ($N^{alpha}$-citraconyl)-arginyl-cholesterol. Cationic lipid arginyl-cholesterol is prepared by esterification of cholesterol with stoichiometric quantity of N(alpha)-tert-butoxycarbonyl (tBOC)-L-arginine in dimethoxyethane in the presence of equimolar amount of 4-dimethylaminopyridine (DMAP) as catalyst, followed by removal of the protective group in 4N HCl/dioxane. After removal of dioxane, arginyl-cholesterol is dissolved in 2,6-diaminopyridine and reacted at 0°-4° C. with citraconic anhydride overnight. ($N^{alpha}$-citraconyl)-arginyl-cholesterol is purified from the reaction mixture by column chromatography on silica in the ascending gradient of methanol in chloroform in the presence of 0.1% diisopropylamine. This lipid has net charge of zero under physiological conditions at neutral pH, but irreversibly produces cationic lipid arginyl-cholesterol (net charge, 2+) upon hydrolysis in mildly acidic medium (pH 4.5-5.5) such as within the endocytotic vesicles of cells.

"Caged" cationic lipid 1,2-dioleoyl-3-(N$^{alpha}$-citraconyl)-arginyl-glycerol. Cationic lipid 1,2-dioleoyl-3-arginyl glycerol is prepared from 1,2-dioleoylglycerol (diolein) and tBOC-arginine, and modified with citraconic anhydride as described above. The resulting lipid 1,2-dioleoyl-3-(N$^{alpha}$-citraconyl)-arginyl-glycerol has net charge of zero at physiological conditions at neutral pH, but irreversibly produces di-cationic lipid 1,2-dioleoyl-3-arginyl-glycerol (net ionic charge, 2+) upon hydrolysis under mildly acidic conditions of pH 4.5-5.5. Similarly, N(alpha)-citraconyl-agrinyl-1,2 diacylglycerols with other fatty acid residues at positions 1 and 2 are prepared.

"Caged" cationic lipid 1,2-diacyloxy-3-citraconylaminopropane. 1,2-di($C_{10}$-$C_{18}$)acyloxy-3-amino-propane is incubated with excess citraconic anhydride in anhydrous 2,6-diaminopyridine at 4-6° C. overnight. The amide product is isolated by column chromatography on silica in ascending gradient of methanol in chloroform containing 0.1% diisopropylamine. This lipid has net charge of −1 (anionic) under neural pH in physiological conditions, but irreversibly forms a cationic lipid 1,2-diacyloxy-3-aminopropane (net ionic charge+1) when exposed to mildly acidic pH, e.g., pH 4.5-5.5 as in cellular endosomes and/or lysosomes.

"Caged" cationic lipid 1,2-dioleyloxy-3-(N,N-dimethyl-N-(2-(N'-citraconylamino)ethyl)ammonio-propane is prepared by citraconylation under similar conditions from a di-cationic lipid 1,2-dioleyloxy-3-(N,N-dimethyl-N-(2-aminoethyl))ammonio-propane. This neutral lipid (net charge zero at neutral pH physiological conditions) irreversibly reverts to di-cationic 1,2-dioleyloxy-3-(N,N-dimethyl-N-(2-aminoethyl))ammonio-propane upon hydrolysis under mildly acidic pH, e.g., pH 4.5-5.5.

"Caged" cationic lipid 1,2-dimyristoyloxy-3-(N,N-dimethyl-N-(2-phosphoryloxy) ethyl)-ammonio-propane. 1,2-dimyristoyloxy-3-(N,N-dimethyl-N-(2-hydroxyethyl))ammonio-propane is reacted overnight at room temperature with excess phosphorus oxychloride in anhydrous pydidine. The reaction mixture is chilled in ice, treated with water, the lipid are extracted with methylene chloride, and the sought compound is isolated by chromatography on silica using ascending gradient of methanol in chloroform. This lipid has net charge of minus 1 at neutral pH, but reverts to cationic, transfection-enhancing lipid, 1,2-dimyristoyloxy-3-(N,N-dimetyl-N-(2-hydroxyethyl))ammonio-propane, by the action of phosphatase enzymes, such as ones present in cellular lysosomes.

"Caged" cationic lipid 1,2-dimyristoyloxy-3-(N,N-dimethyl-N-(2-dithiocarbonyloxy)ethyl)ammonio-propane. 1,2-dioleyloxy-3-(N,N-dimethyl-N-(2-hydroxyethyl))ammonio-propane is stirred for 4 hours with excess carbon disulfide and finely ground potassium hydroxide in anhydrous tetrahydrofuran at room temperature. The reaction mixture is poured into water-ice mixture, and extracted with methylene chloride. The extract is dried over anhydrous sodium sulfate, and the sought compound is isolated by chromatography on silica using ascending gradient of methanol in chloroform. This lipid has zero net charge and is stable at neutral pH, but loses its dithiocarbonate (xanthogenate) group through elimination reaction, and reverts to cationic, transfection-enhancing lipid, 1,2-dioleyloxy-3-(N,N-dimethyl-N-(2-hydroxyethyl))ammonio-propane, when exposed to lower pH (e.g., pH 4.5-5.5), such as one present in cellular endosomes and/or lysosomes.

The same exemplary synthetic approaches can be employed to prepare "caged" cationic lipids from parent quaternary ammonium compounds such as N,N-di(C12-C18)-alkyl-N-methyl-N (hydroxyalkyl)ammonium halides and N,N-di(C12-C18)-alkyl-N-methyl-N-(aminoalkyl)ammonium halides by modification of hydroxy- or amino-groups of these compounds in the above-described manner. These parent compounds are known in the art to be transfection-enhancing lipids (U.S. Pat. No. 6,333,433; U.S. Pat. No. 5,994,317).

Similarly, "caged" cationic polymers are prepared from amino-group containing cationic polymers by reaction with citraconic anhydride in pyridine, and used to make transfection-enhancing compositions such as GENOSPHERES.

"Caged" charge-changing compounds described herein can be used in any delivery system, in particular, in a nucleic acid delivery system, that normally comprises cationic lipids and/or polymers, wherein a portion or all of the lipid or polymer is "caged" charge-changing lipid or polymer. In the GENOSPHERES, "caged" charge-changing lipids with an overall neutral or anionic charge would replace a portion, or all, of the vesicle-forming non-cationic lipids; if the overall charge of a "caged" charge-changing lipid is positive, it may replace a portion of, or all of the cationic lipid content of the GENOSPHERE. Therefore, until the target cell or tissue, i.e. the cell or tissue containing cells to be transfected, is reached, the GENOSPHERE administered into a subject will maintain lower level of positive charge reducing its destabilizing interactions with plasma proteins and non-specific phagocytic clearance from the body. Upon reaching the target cell where charge-changing factor is present, for example, acidic pH in the intracellular endosomal or lysosomal compartment, or by action of the tissue enzyme present extracellularly in the target tissue, the amount of transfection-enhancing cationic lipid in such GENOSPHERE will advantageously increase.

12. Formulation and Administration of GENOSPHERES

For administration to a subject or application onto cells, GENOSPHERES of the invention can be advantageously formulated in a biocompatible liquid medium, more preferably an aqueous solution. In regard to its function, the medium is preferably a pharmacologically acceptable medium. Such pharmacologically acceptable media are known to those skilled in the art. Such formulation can be achieved by a variety of methods known in the art. Examples of such methods are, without limitation, dialysis, ultrafiltration, tangential flow filtration, and gel-chromatography.

The produced composition that can be deep frozen or freeze-dried for better storage. In this case it is preferable that the composition also contains a cryopreservant, such as a sugar, a polyol, or a hydrophilic polymer. Suitable cryopreservants are, without limitation, glucose, sucrose, trehalose, maltose, mannose, lactose, mannitol, glycerol, polyvinylpyrrolidone (PVP), polyvinyl alcohol (PVA), polyacrylamide (PAA), FICOLL (cross-linked sucrose polymer), dextran, polyethylene glycol, and polypropylene glycol. It was unexpectedly found that GENOSPHERES of the invention remain transfectionally active and disaggregated after reconstitution from the lyophilizate.

GENOSPHERES can be administered to the cells by any method known in the art. For in vitro processes, GENOSPHERES are typically added to the cultures containing cells in which a nucleic acid is to be delivered. Cell entry of GENOSPHERES may be assisted by administration of certain membrane-active compounds, such as poly(ethylene glycol), or by physical stimuli, such as, electric discharge. For administration in a living organism, such as a patient's body, e.g. for medical purposes, GENOSPHERES can be administered parenterally by injection, for example, intravenously, intraarterially; or into an enclosed body cavity; topically onto the skin or into a body cavity that communicates with the exterior; or orally. Formulations for such administration methods are known to skilled in the art. Because of the protection that GENOSPHERES afford against nucleic acid-degrading enzymes, oral administration is possible. As a result, GENOSPHERES are likely to enter enteric lymphoid structures, such as Peyer patches and mesenteric lymph nodes, where they may act as DNA vaccines to elicit immune response against proteins encoded by the GENOSPHERE-encapsulated DNA.

13. Using Solubilizing, Nucleic Acid-Condensing, Non-Cationic Substances.

While the disclosed methods describe making GENOSPHERES using water-miscible organic solvents effecting molecular and/or micellar dissolution of the particle-forming agents, it is noted that in some instances, certain non-cationic substances with high solubility in water, can be used instead, or in addition to, the organic solvent. Advantageously, such non-cationic, solubilizing substances also effect condensation of nucleic acid molecules. Preferably such non-cationic, solubilizing substance is present at a concentration at which it is substantially molecularly dissolved, but effective to solubilize the particle-forming agent, e.g. lipid, into a micellar or molecular form. It is not necessary for this solubilizing substance to be a detergent, i.e. to be predominantly micellarly dissolved by itself. Thus, the invention provides for methods of making GENOSPHERES using aqueous solutions of such non-cationic, solubilizing substances. The methods comprise the steps of: (i) combining a nucleic acid and a particle-forming agent in an aqueous solution of a non-cationic, solubilizing substance wherein said particle-forming component is solubilized into micellar or molecular form, and optionally (ii) reducing the amount of said solubilizing substance to effect formation of nucleic-acid containing particles. The particle-forming component comprises a lipid, a particle-forming polymer, or a combination of both. Typically, a nucleic acid and a particle-forming agent are combined in a solution containing from about 1% to about 90% of a solubilizing substance, more preferably, from about 5% to about 80% of a solubilizing substance, most preferably from about 5% to about 60% of a solubilizing substance by weight. Such solubilizing non-cationic substance is, for example, a hydrophilic polymer or a polyol. Preferred hydrophilic polymers are poly(ethylene glycol), poly(propylene glycol), poly(vinyl pyrrolidone), poly(acrylamide), polyvinyl alcohol, dextran and other poly(anhydrohexoses), co-polymers thereof, or derivatives thereof. Preferred polyols are sugars (sucrose, fructose, lactose), solid polyalcohols (erythritol, treitol, sorbitol, mannitol, glucitol) and derivatives thereof. The hydrophilic polymers typically are in the molecular weight range from about 400 to about 2,000,000. One particularly preferred non-cationic, nucleic acid-condensing hydrophilic polymer is poly(ethylene glycol). Poly(ethylene glycol) is known to condense nucleic acids as well as to solubilize hydrophobic compounds, such as lipids, in aqueous solutions (Lerman, Proc. Natl. Acad. Sci. USA 68:1886-1890; Louie and Server, J. Mol. Biol. 242:547-558 (1994)). Poly(ethylene glycol) with molecular weight from about 200 to about 2,000, 000 is suitable, while the range of 400-20,000 is preferred.

To make GENOSPHERES according to the present invention using non-cationic, solubilizing substances one may use the same methods as described herein, substituting a non-cationic, solubilizing substance, e.g. a hydrophilic polymer or a polyol, for all or part of the water-miscible organic solvent. To reduce the amount of a non-cationic, solubilizing substance after combining nucleic acid and a particle forming agent, the methods based on dialysis, ultrafiltration, or size exclusion are preferred. The resulting GENOSPHERES are formulated and utilized as described in previous sections herein.

14. Making Lipid-Encased Nucleoproteins and Viruses.

It is recognized that the present invention is applicable to encapsulation of nucleoproteins, including wholly or partially assembled viral particles, into lipid bilayers. While viruses are naturally adapted, highly efficient vectors for transfection of their nucleic acids into their host cells, viruses as medical gene delivery vectors are hindered by the body immune reaction, suffer from degradation by the body enzymes, and are limited to the cells to which the viruses have natural affinity. These drawbacks can be overcome if viruses are encapsulated, for example, into lipid bilayers shielding them from the subject's body environment. Methods for encapsulating viruses into lipid bilayers are known in the art. They include passive entrapment into lipid bilayer-enclosed vesicles (liposomes), and incubation of virions with liposomes (U.S. Pat. No. 5,962,429; Fasbender, et al., J. Biol. Chem. 272:6479-6489; Hodgson and Solaiman, Nature Biotechnology 14:339-342 (1996)). The GENOSPHERE formulation methods using organic-aqueous monophase of the present invention are suitable for high yield, high efficiency encasing of virions (viruses) into one or more lipid bilayers of desired composition. Without being limited by a theory, we assume that acidic proteins exposed on the surface of a virion provide an interface for complexation with the cationic lipid/cationic polymer component of the GENOSPHERE and serve as a "scaffold" for the bilayer formation by the neutral lipid component. Exemplary types of viruses are adenoviruses, retroviruses, herpesviruses, lentiviruses, and bacteriophages. Preferred classes of viruses for GENOSPHERE encapsulation are adenoviruses and adeno-associated viruses. All of the above-described techniques for GENOSPHERE formulation are generally suitable for viral encapsulation, a virus being substituted for the nucleic acid. Because the virion size is generally larger than that of a nucleic acid molecule, the amount of lipid in a virus-encapsulating GENOSPHERE is preferably reduced to accommodate only one to a few bilayers on the viral surface. A skilled artisan would easily choose the amount of lipid for a particular virion based on the bilayer surface areas per lipid molecules tabulated in the known reference books (e.g., Marsh, Handbook of Lipid Bilayers). It is especially advantageous to use ligand-targeted GENOSPHERE methods for virion encapsulation as it allows to change the natural tropism of a virus to one desired by the particular therapy or other application. The desirability of changing the natural viral tropism to target certain pathological cells is recognized in the art (see, e.g., U.S. Pat. No. 6,060,316).

EXAMPLES

Example 1

This example illustrates a method for preparing GENOSPHERES using solvent-condensed nucleic acids in the mixtures of alcohol and aqueous solvents. A pUC-derived bacterial plasmid DNA having luciferase reporter gene under CMV early promoter (pCMVLuc, 100 µg) was dissolved in the mixture of ethanol and 5% aqueous dextrose solution (1:1 by volume, 500 µl) and heated to 50° C. Cationic lipid (DDAB, 600 nmol) and neutral lipids (POPC 1.2 micro-mol, PEG-DSPE, 6 nmol) were mixed in chloroform solution and dried by rotary evaporation. The dried lipids were dissolved in ethanol (250 µl) and subsequently mixed with 5% aqueous dextrose (250 µl). The lipid solution in ethanol:5% aqueous dextrose (1:1) was then heated to 50° C., the DNA solution was rapidly injected into the lipid solution, and mixed by rapid pipetting for several seconds. This method prepares lipid-DNA complexes in a monophase of ethanol and water. The ethanol was subsequently removed by rotary evaporation or dialysis against deionized distilled water. The resulting particles include >95% of DNA by the dye accessibility assay using Pico-Green DNA dye (Molecular Probes, Inc.) and have a size distribution (as determined by dynamic light scattering) ranging from 120 to 350 nm in diameter.

Example 2

This example illustrates a modification of the method described in example 1 where the condensed DNA is first added to dry films of cationic lipid, followed by coating with neutral lipids. In this method, pCMVLuc plasmid DNA (100 µg) was dissolved in the mixture of ethanol and a 5% dextrose aqueous solution (1:1 by volume, 1 ml) and heated to 55° C. The cationic lipid (DDAB, 100 µg) in chloroform was dried by rotary evaporation on the bottom of a glass vial. The monophase solution of DNA was then added to the dried cationic lipid phase and agitated until the lipid was transferred into solution and combined with DNA forming cationic lipid-DNA complexes with no signs of visible aggregates. In a second vial, neutral lipids (POPC:PEG-DSPE, 1.2 micromol, and PEG-DSPE 6 nmol) were deposited as a film from an organic solution by rotary evaporation. The cationic lipid-DNA complexes in the ethanol:5% dextrose monophase (1 ml) were subsequently injected into the vessel containing the dried neutral lipid and agitated at 55° C. to effect transfer of the neutral lipid into solution. The ethanol was then removed by rotary evaporation or by dialysis against deionized water. The resulting particles had a size distribution ranging from 75 to 250 nm.

Example 3

This example illustrates a method for isolating GENOSPHERES using a sucrose density gradient. Five ml clear ultracentrifuge tubes (13×51 mm) were filled with a 15% sucrose solution (3.5 ml) and subsequently subjected to six or more cycles of alternating freezing and thawing to form a continuous sucrose density gradient (0-30% sucrose, 1-1.127 g/ml). The complexes were layered on top of the gradient and then centrifuged at 212,000×g for 4-16 hours at 4° C. using a Beckman SW 50.1 swinging-bucket rotor. Free lipid was extracted from the top of the gradient, free DNA from the bottom, and the complexes were recovered from a sharp band corresponding to the density between 1.04 and 1.06 g/mL, typically between 1.046 and 1.055 g/mL.

Example 4

Cationic lipid-plasmid DNA GENOSPHERES were prepared according to Example 1, except that the following cationic lipids were substituted for DDAB: 1,2-dioleoyl-3-trimethylammono-propane chloride (DOTAP); 1,2-dioleoyl-sn-3-glycero(ethylphosphoryl)-choline (DOEPC); 1,2-dimyristoyl-sn-3-glycero(ethylphosphoryl)-choline (DMEPC); 1-palmitoyl-2-oleoyl-3-glycero(ethylphosphoryl)-choline (POEPC); 1,2-distearoyl-3-glycero(ethylphosphoryl)-choline (DSEPC); N-agrinyl-1,2-dioleoylphosphatidylethanolamone (Arg-DOPE). The resulting DNA-lipid particles had the same characteristics as in Example 1.

Example 5

Cationic lipid-plasmid DNA GENOSPHERES were prepared according to Example 2, except that N-agrinyl-1,2-dioleoylphosphatidylethanolamone (Arg-DOPE) was substituted for DDAB. The resulting DNA-lipid particles had the same characteristics as in Example 2.

Example 6

Cationic lipid-plasmid DNA GENOSPHERES were prepared according to Example 2, except that cholesterol imidazole derivative (CHIM) was added to neutral lipid component according to the following proportions (per microgram of plasmid DNA): DDAB, 600 nmol; POPC, 1500 nmol; CHIM, 1000 mmol; PEG-DSPE, 6 mmol. The resulting cationic-neutral lipid-plasmid DNA GENOSPHERES had the same characteristics as in Example 2.

Example 7

Cationic lipid-plasmid DNA GENOSPHERES were formed by the method described in Example 2 except cholesterol (Chol) was added to POPC as the neutral lipid component of the mixture according to the following proportions (per microgram of plasmid DNA) DDAB, 600 nmol; POPC 1500 nmol; Chol, 1000 nmol; PEG-DSPE, 6 nmol. The resulting GENOSPHERES has the same characteristics as in Example 2.

Example 8

Cationic lipid-plasmid DNA GENOSPHERES were formed by the method described in Example 1 except that 1,2-dipalmitoyl-3-sn-phosphocholine (DPPC) or 1,2-distearoyl-3-sn-phosphocholine (DSPC) was used instead of POPC as the neutral lipid component of the mixture according to the following proportions (per microgram of plasmid DNA) DDAB, 600 nmol; DPPC or DSPC, 1500 nmol; Chol, 1000 nmol; PEG-DSPE, 6 nmol. The resulting GENOSPHERES have the same characteristics as in Example 1.

Example 9

Lipid-plasmid DNA GENOSPHERES were formed by the method described in Example 2 except that dioxane, ethylene glycol dimethyl ether, or tertiary butanol were used instead of ethanol to form lipid- and DNA-solubilizing aqueous-organic monophase. The resulting GENOSPHERES have the same characteristics as in Example 1.

Example 10

Lipid-plasmid DNA GENOSPHERES were formed by the method described in Example 1 except that methanol was substituted for ethanol in the aqueous-organic monophase. The resulting GENOSPHERES have the same characteristics as in Example 1.

Example 11

Folate-targeted lipid-plasmid DNA GENOSPHERES were formed according to Example 1 by incorporation of folate-PEG-DSPE (1 mol % of total neutral lipids) into the neutral lipid mixture prior to chloroform removal. The transfection efficiency of folate-targeted GENOSPHERES in folate receptor-overexpressing human nasopharyngeal cancer cells (KB31 and KB85 cell lines, ATCC) was several fold greater than that of non-targeted GENOSPHERES.

Example 12

Lipid-DNA GENOSPHERES targeted to HER2 receptor were formed by incorporation of PEG-DSPE terminally attached to a highly internalizable, recombinant anti-HER2 singe chain Fv antibody fragment F5. The micellar aqueous solution of F5-PEG-DSPE was incubated with preformed-non-targeted GENOSPHERES at 55° C. for 30 min. Non-targeted GENOSPHERES were prepared as described in Example 1. The transfection efficiency of HER2-targeted GENOSPHERES in HER2-overexpressing human breast cancer cells (SK-Br-3, BT-474, from the American Type Culture Collection) was 32-fold greater than that of non-targeted GENOSPHERES, while in a cell line having low HER2 expression (MCF-7, ATCC) the transfection efficiency of HER2-targeted and non-targeted GENOSPHERES was the same.

Example 13

Lipid-DNA GENOSPHERES were formed by the method described in Example 2 but included a 19-base phosphorothioate oligonucleotide instead of plasmid DNA. The resulting lipid-oligonucleotide particles had the same characteristics as those in Example 2.

Example 14

Determination of the aqueous space of GENOSPHERES using $^{14}C$-sucrose. Lipid-plasmid DNA GENOSPHERES were formed according to the method described in Example 2 from plasmid DNA and contained the following lipids, per 1 microgram of DNA: with added fluorescent lipid Rhodamin-PE. The composition was: DDAB, 600 nmol; hydrogenated soy phosphatidylcholine (HSPC), 1200 nmol; PEG (M.w. 2,000)-DSPE, 6 nmol; Chol, 600 nmol; fluorescent-labeled lipid Rhodamin-PE, 100 nmol. GENOSPHERES were formed in the presence of $^{14}C$-labeled sucrose as an aqueous space marker. The GENOSPHERES were separated from the solution using size-exclusion chromatography on a 4% agarose gel (Sepharose 4B, Amersham Pharmacia Biotech) column, the sucrose entrapped within the internal aqueous space of GENOSPHERES was quantified by radioactivity counting, and the volume of interval aqueous space was calculated. The internal aqueous space within GENOSPHERES was 15-25% of the theoretical internal aqueous space geometrically calculated for the lipid vesicles of similar size.

Example 15

Formation of GENOSPHERES at various amounts of organic solvent. DDAB (1.2 μmol), cholesterol (0.8 μmol), POPC (2.4 μmol) and fluorescent cationic lipid DiIC18(3) (N,N-bis-hexadecyl-indocarbocyanin dihydrochloride, Molecular Probes, Inc., Oregon, USA) (0.0044 μmol) were dissolved in the first volume (V1) of 100% ethanol to form a PFC solution. Plasmid pCMVLuc (0.2 mg) was dissolved in the second volume (V2) of 5% aqueous dextrose form a NAC stock solution. The NAC and PFC solutions were mixed at 55° C. and incubated for 10 min. The mixtures were brought to room temperature, and ethanol was removed by overnight dialysis through regenerated cellulose membrane (mol. weight cut-off 12-14,000 D) against 1 L of 150 mM sodium chloride in distilled water. Grossly precipitated material, if any, was removed by gravity sedimentation overnight and decanting. The decanted fluid containing precipitation-stable PFC-NAC microparticles were stored at 4-6° C. for 17 days. Then the size of NAC-PFC particles in decanted samples was determined by quasielastic light scattering (Nicomp C-370 particle size analyzer) using Gaussian size distribution analysis. The amount of NAC encapsulated into precipitation-stable microparticles was determined by fluorescent dye binding assay (PicoGreen, Molecular Probes, Inc., Oregon, USA) according to manufacturer's specifications, after solubilization of the particles in the presence of 0.5% zwitterionic detergent ZWITTERGENT 3-14 (Fluka, USA), 5% DMSO. The amount of PFC in the particles was determined from the DiIC8(3) fluorescence (excitation at 550 nm; emission at 565 nm) on a Fluorolog-2 photon-counting spectrofluorometer (Joben-Yvon, France), using standard curve method. The results are summarized in the following table:

| $V_1$, mL | $V_2$, mL | % ethanol by volume | Particle size (average ± standard deviation) | % NAC encapsulated |
|---|---|---|---|---|
| 0.1 | 0.9 | 10% | 756 ± 332 | 86.5% |
| 0.2 | 0.8 | 20% | 318 ± 145 | 89% |
| 0.3 | 0.7 | 30% | 190 ± 80 | 95.6% |
| 0.4 | 0.6 | 40% | 174 ± 80 | 77.9% |
| 0.5 | 0.5 | 50% | 220 ± 110 | 83.1% |
| 0.6 | 0.4 | 60% | 208 ± 143 (partial precipitation) | 58.2% |
| 0.7 | 0.3 | 70% | Complete precipitation | 0 |

Characterization of GENOSPHERES
1. Density Determination of GENOSPHERES in Sucrose Gradient Centrifugation.

The sucrose gradient centrifugation technique is described by Xu, et al., Biophys. J., v. 77, p. 341-351 (1999).

Table 1 illustrates the apparent bouyant density of plasmid DNA-containing GENOSPHERES determined on sucrose gradient centrifugation. The sample was layered on a continuous linear sucrose gradient, 0-35% sucrose, and was centrifuged at 4° C. for 16 h. A single thin band, which contained DNA representing the final purified GENOSPHERES product, formed at 12-14% sucrose, corresponding to the density of 1.0465-1.0549 g/cc. The particle size was determined by dynamic light scattering. Analyses of DNA and lipids in the GENOSPHERES recovered from the gradient show the composition to contain DDAB and POPC in the ratio of 3.7:7.3 (nmol:nmol) per micro-g of DNA.

| GENOSPHERE lipid composition (nmol lipid per micro-g DNA) | Band width/ gradient height | Mean density, g/ml | Mean particle size, nm |
|---|---|---|---|
| DDAB/CHIM/POPC 6:4.8:7.2 | 0.80/4.2 cm | 1.0465 | 186 |
| DDAB/CHIM/POPC 6:4.8:7.2, lyophilized with mannitol and reconstituted | 0.35/4.2 cm | 1.0549 | 187 |
| DOTAP/CHIM/POPC 6:4.8:7.2 | 0.35/4.2 cm | 1.0507 | 66 |
| DDAB/POPC 6:12 | 0.30/4.2 cm | 1.0549 | 47 |

Table 2 shows the recovery (based on DNA) and size of plasmid DNA-containing GENOSPHERES after sucrose density gradient purification in another experiment. GENOSPHERES recovery was over 75% and the particle size ranged from 40 to 170 nm.

TABLE 2

| GENOSPHERE lipid composition (nmol lipid per micro-g DNA) | Recovery, % | Particle size, nm |
|---|---|---|
| DDAB/POPC 6:12 | 74 | 50–170 |
| DDAB/CHIM/POPC 6:4.8:7.2 | 77 | 105 ± 20 |
| DSPC-E/DOPE 12:12 | 93 | 40–150 |
| DSPC-E/CHIM/DOPE 12:6:12 | 76 | 40–160 |
| DOPC-E/CHIM/DOPE 12:6:12 | | 90 ± 10 |

2. Freeze-Fracture Electron Micrographs of GENOSPHERES

Figure 2:
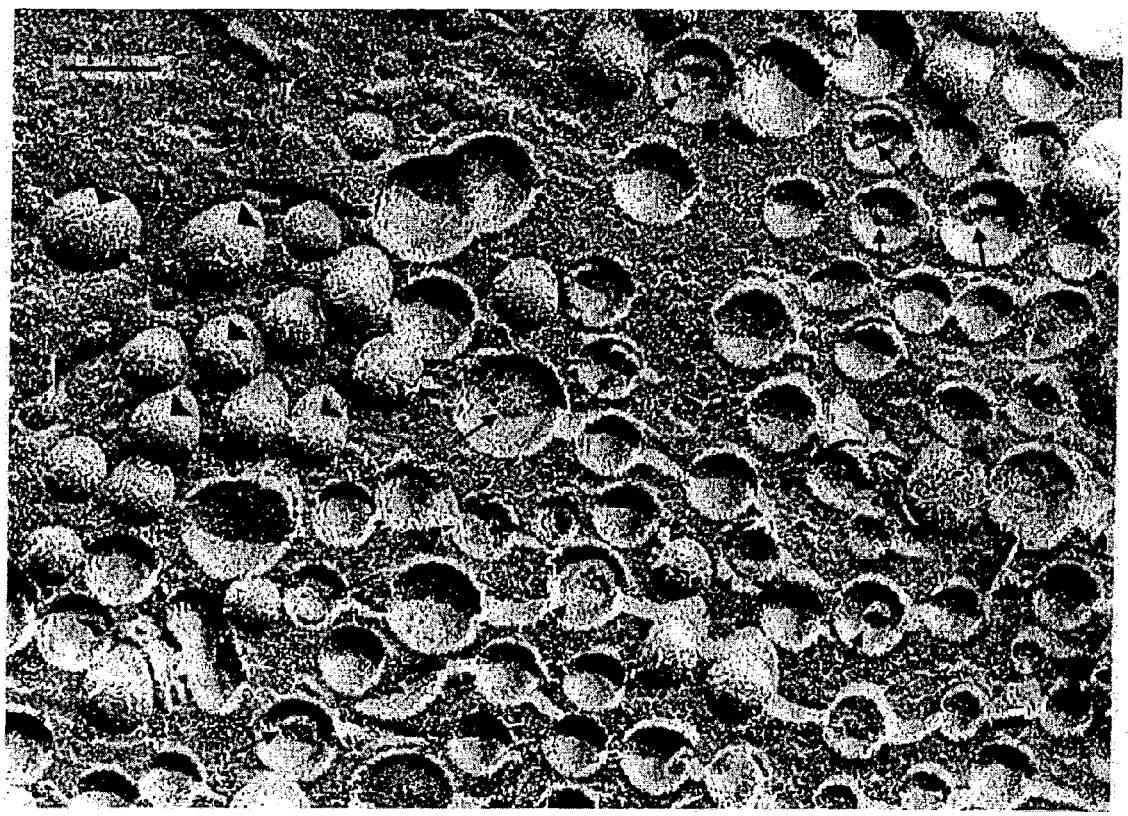
FIG. 2 represents freeze-fracture electron microscopic image of the GENOSPHERES composed of DDAB/Cholesterol/POPC (6/6/12 nmoles per micro-g of plasmid DNA). Arrowheads point to the smooth fracture planes indicative of a bilayer surrounding the particle core. Arrows point to the fracture plane "jump" indicative of a non-bilayer structure of the nucleic acid-containing core.

The freeze-fracture electron microscopic image of GENOSPHERES composed of DDAB/Cholesterol/POPC/PEG-DSPE (6/6/12/0.12 nmoles per micro-g DNA) is shown in FIG. 1. FIG. 2 shows the freeze-fracture electron microscopic image of the GENOSPHERES from DDAB/Cholesterol/POPC (6 16 12 nmoles per micro-g DNA). Both images show similar structures having a smooth surface fracture plane and a homogeneous size distribution.

FIG. 2 reveals the structure of lipid layer and DNA core. The smooth convex fracture surface (arrow heads) exposed corresponds to the hydrophobic end of the inner half of lipid bilayer which may contain mostly cationic lipid interacting with DNA in the core. Numerous concave surfaces (arrows) show jump of fracture line that is likely the break of a weak region of DNA-cationic interaction.

3. Stability of Nucleic Acid within GENOSPHERES Against DNase

Plasmid DNA alone ("naked" DNA), plasmid-liposome complexes and GENOSPHERES were treated with DNase either in the absence or in the presence of surfactant sodium dodecylsulphate (SDS), and the digested DNA were viewed after electrophoresis on a 0.8% agrose gel with ethidium bromide staining. Table 3 shows the degree of digestion of DNA by DNase as estimated from the gels. No intact DNA remained in the DNA alone lane. Plasmid-liposome complexes were partially protected by lipids. In contrast, GENOSPHERES of different compositions had their DNA completely protected by lipids.

TABLE 3

| Composition (lipids, nmol per micro-g of DNA) | % DNA digested, no SDS | % DNA digested, with SDS |
|---|---|---|
| DNA only | 70–100% | 70–100% |
| DNA complexed with preformed liposomes of DDAB and DOPE (12:12) | 30–50% | 70–100% |
| GENOSPHERES: | | |
| DDAB/POPC 6:12 | <10% | 30–50% |
| DDAB/POPC 6:12 lyophilized with mannitol and reconstituted | <10% | 30–50% |
| DDAB/CHIM/POPC 6:4.8:7.2 | <10% | 30–50% |
| DDAB/CHIM/POPC 6:4.8:7.2 lyophilized with mannitol and reconstituted | <10% | 30–50% |

4. In Vitro Cytotoxicity of Gene Carriers

Figure 3:
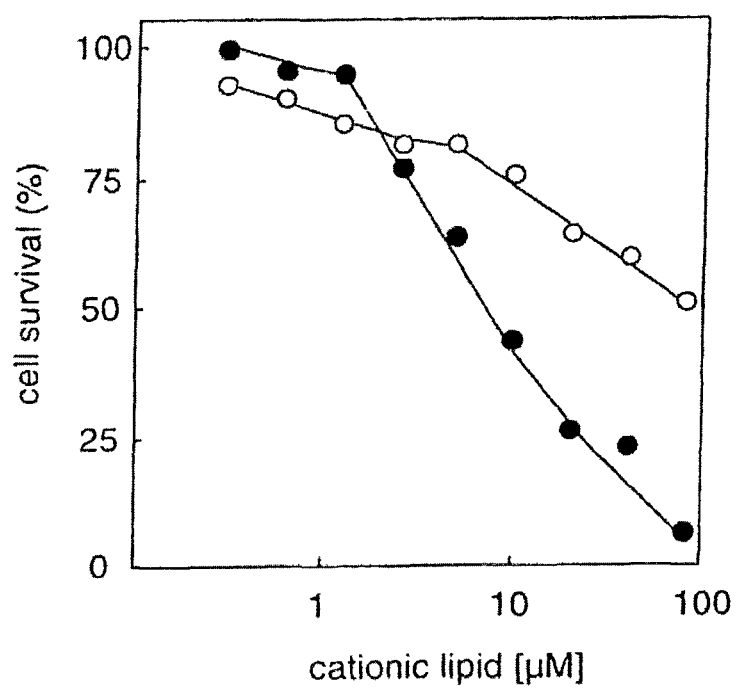
FIG. 3 demonstrates the effect of increasing concentration of traditional plasmid-lipid complexes containing 12 nmol DDAB and 12 mmol DOPE per micro-g DNA (filled circles) and GENOSPHERES containing 6 mmol DDAB, 4.8 mmol CHIM, and 7.2 nmol POPC per micro-g DNA (hollow circles), on the viability of SK-Br-3 cells in vitro.

Cationic lipids are known to alter membrane integrity by binding to negative membrane components. Such strong binding of clustered charges on membranes may cause irreparable defects in membranes, leading to cell death. SK-Br-3 cells were exposed to plasmid-liposome complexes prepared by mixing of pUC-derived bacterial plasmid with DDAB/DOPE small unilamellar liposomes, or to GENOSPHERES, for 5 hours in a growth medium, and post-incubated in fresh medium for 80 hours. Cell viability was assessed by a conventional tetrazolium assay. As shown on FIG. 3, DDAB/DOPE plasmid-liposome complexes had an $IC_{50}$ (50% cytotoxic dose) of 9 micro-M DDAB, while GENOSPHERES made with DDAB/CHIM/POPC (6:4.8:7.2) were significantly less cytotoxic in these cells, with an $IC_{50}$ of 90 micro-M DDAB.

5. In Vitro Transfection

Table 4 compares the transfection efficiency in terms of expression of the marker gene, in this case luciferase (in ng luciferase per mg cell protein), of GENOSPHERES versus traditionally prepared plasmid-liposome complexes. SKBr-3 cells were plated at 100,000 cells/well in 24-well plates 24 h before transfection, GENOSPHERES with encapsulated plasmid DNA having a luciferase gene under the control of CMV early promoter were added at 1.0 μg of DNA per well and allowed to incubate for 6 h in 1 ml of the cell growth medium containing 10% serum. The medium with GENOSPHERES was then removed, and the cells were incubated in the fresh growth medium for 24 hours. The amount of luciferase produced by the cells was determined in cell lysates by luminometry using luciferin-ATP method, and standardized against commercial preparation of firefly luciferase (Boehringer Mannhein AG). The amount of cell protein was determined by the dye binding method of Bradford using commercial kit (Bio-Rad). Both GENOSPHERES and plasmid-lipid complexes had the same lipid composition, DDAB/CHIM/POPC/mPEG-DSPE (6 nmol:4.8 nmol:7.2 nmol:0.06 nmol per micro-g DNA). Despite having the same lipid composition, GENOSPHERES produced higher levels of transfection that plasmid-lipid complexes prepared by incubation of preformed liposomes with plasmid DNA. HER2-targeted GENOSPHERES and plasmid-lipid complexes were prepared by co-incubation of GENOSPHERES or plasmid-lipid complexes with anti-HER2 Fab-PEG-DSPE conjugate, resulting in the capturing of the Fab-PEG-lipid conjugate into the surface lipid layer of the GENOSPHERES or within the lipid component of plasmid-lipid complexes. The reconstituted sample of lyophilized GENOSPHERES is noted to be the most active in terms of transfection. A superior transfection efficiency of GENOSPHERES comparing to plasmid-liposome complexes of the same lipid composition is also demonstrated. Marker gene expression (Luciferase) of GENOSPHERES was 65-fold greater than for traditional plasmid-lipid complexes. The reconstituted lyophilized GENOSPHERES elevate expression further to 300-fold that of targeted traditional complexes. Anti-HER2 Fab'-targeted GENOSPHERES increase transfection efficiencies in HER2-overexpressing cells 10-fold relative to the non-targeted system in each formulation.

TABLE 4

| Formulation | Without targeting | With HER2-directed targeting |
|---|---|---|
| Plasmid-liposome complex | 0.067 ± 0.005 | 0.86 ± 0.05 |
| GENOSPHERES | 4.4 ± 0.1 | 55 ± 8 |
| GENOSPHERES lyophilized and reconstituted | 31 ± 2 | 259 ± 31 |

Table 5 shows in vitro targeting of various anti-HER2 immuno-GENOSPHERES to the HER2 receptor-expressing SKBr-3 cells. Immuno-GENOSPHERES which consist of anti-HER2 Fab' antibody fragment on the surface of GENOSPHERES were prepared by co-incubation of GENOSPHERES with anti-HER2 Fab-PEG-DSPE conjugate, resulting in the capturing of the Fab-PEG-lipid conjugate into the surface lipid layer of the GENOSPHERES. The surface-attached anti-HER2 antibody fragment induces endocytosis of the GENOSPHERES and thus introduction of the plasmid to an interior localization in the cell. The attachment of targeting ligand increased the transfection level 4-37-fold.

TABLE 5

| Lipid composition (nmol lipid ratio/μg DNA) | Luciferase activity (ng/mg protein) | |
| --- | --- | --- |
| | Non-targeted | Targeted with anti-HER2 Fab' |
| DDAB/CHIM/DOPC/mPEG-DSPE (6:4.8:7.2:0.06) | 24.20 | 230.8 |
| DDAB/CHIM/EggPC/mPEG-DSPE (6:4.8:7.2:0.06) | 26.02 | 105.9 |
| DDAB/CHIM/POPC/mPEG-DSPE (6:4.8:7.2:0.06) | 10.86 | 414.2 |

It has been well established that an in vitro transfection system made of cationic liposome-DNA complexes containing phosphatidylethanolamine as a "helper" lipid has higher transfection efficiency in cultured cells. In contrast to a general belief that the cationic liposome-DNA complexes consisting of phosphatidylcholine instead of phosphatidylethanolamine as the "helper" lipid have a very low in vitro transfection efficiency, GENOSPHERES which are prepared by this invention have an unexpectedly high in vitro transfection efficiency, despite having phosphatidylcholine and no phosphatidylethanolamine. This illustrates that the polymorphic nature of phosphatidylethanolamine is not required to have high transfection activity in the GENOSPHERE delivery system based on cationic lipids.

Table 6 shows expression of luciferase (ng/mg of cell protein) by SKBr-3 cells transfected with the plasmid DNA carrying marker luciferase gene (under the control of early CMV promoter) using plasmid-liposome complexes in comparison with GENOSPHERES and reconstituted lyophilized GENOSPHERES. The choice of the water-miscible organic solvent was not limited to ethanol; t-butanol and methanol were suitable as well. In the absence of lyophilization, transfection activity of plasmid-liposome complexes was only 10% of GENOSPHERES with same lipid composition as plasmid-liposome complexes. GENOSPHERES lyophilized in the presence of cryoprotectants, such as sucrose, mannitol or trehalose show higher transfection activity.

In Vivo Transfection.

Table 7 shows Luciferase expression in H157 human lung cancer xenografts in immunodeficient nude mice 24 hours after a single peritumoral injection of plasmid DNA containing luciferase marker gene formulated in plasmid-liposome complexes or GENOSPHERES of different lipid compositions (100 micro-g DNA per injection). The tumors having size of 0.2-1.0 cubic cm were developed subcutaneously after implantation of cancer cells. The data of parallel experiments are presented (separated by commas). The conventional lipid-based gene carriers, such as plasmid-liposome complexes (DDAB/Chol 12:12), that carry excess positive charges, gave a very high expression in lung but not in tumor. The non-specific transfection activity of GENOSPHERES in lung is greatly reduced due to considerably reduced exposure of cationic lipid in these preparations. GENOSPHERES containing small amounts of PEG-DSPE appear to further reduce transfection in lung. The results demonstrate a clear overall trend that GENOSPHERES give higher transfection in tumor in comparison with plasmid-liposome complexes in addition to substantial specificity for the desired tissue. Like in cultured cells, reconstituted lyophilized GENOSPHERES consistently afford more than 10-fold greater marker gene expression relative to non-processed GENOSPHERES.

TABLE 7

| Lipid composition (lipid in nmol per micro-g DNA) | Luciferase expression (pg/mg tissue protein) | |
| --- | --- | --- |
| | tumor | lung |
| GENOSPHERES: | | |
| DDAB/CHIM/POPC (6:4.8:7.2) | 1.10, 7.20 | 0.13, 0.26 |
| DDAB/Chol/POPC/mPEG-DSPE (6:6:6:0.12) | 0.26, 0.66 | 0.08, 0.03 |
| DDAB/CHIM/Chol/POPC/mPEG-DSPE (6:4.8:6:0.12) | 1.69, 2.91 | 0.06, 0.07 |
| DOTAP/CHIM/POPC (6:4.8:7.2) | 0.13, 7.01 | 0.28, 1.04 |

TABLE 6

| Formulation and lipid composition (nmol lipid per micro-g of DNA) | Organic-aqueous monophase solvent[a] | Cryoprotectant | | | |
| --- | --- | --- | --- | --- | --- |
| | | none | Sucrose | mannitol | trehalose |
| GENOSPHERES: | | | | | |
| DDAB/CHIM/POPC (6:4.8:7.2) | ethanol | 61 ± 12 | 338 ± 11 | 74 ± 6 | 89 ± 20 |
| DDAB/CHIM/POPC (6:4.8:7.2) | t-butanol | 78 ± 10 | 54 ± 3 | 181 ± 20 | 240 ± 18 |
| GENOSPHERES (lyophilized and reconstituted): | | | | | |
| DDAB/CHIM/POPC (6:4.8:7.2) | t-butanol | | 109 ± 2 | 162 ± 9 | 414 ± 60 |
| DOTAP/CHIM/POPC (6:4.8:7.2) | t-butanol | | 480 ± 18 | 438 ± 2 | 692 ± 1 |
| Plasmid-liposome complexes: | | | | | |
| DDAB/CHIM/POPC (6:4.8:7.2) | None | 2.8 ± 0.3 | | | |
| DOTAP/CHIM/POPC (6:4.8:7.2) | None | 7.8 ± 1.0 | | | |

[a]Mixed with 5% aqueous dextrose, 1:1 by volume

TABLE 7-continued

| Lipid composition (lipid in nmol per micro-g DNA) | Luciferase expression (pg/mg tissue protein) | |
|---|---|---|
| | tumor | lung |
| DDAB/CHIM/POPC (6:4.8:7.2) (lyophilized and reconstituted) | 1.84, 3.59, 14.6 | 0.19, 3.40, 2.70 |
| DOTAP/CHIM/POPC (6:4.8:7.2) | 31.15, 14.01 | 10.68, 0.56 |
| Plasmid-liposome complexes: | | |
| DDAB/Chol (12:12) | 0.88 | 390.0 |

Table 8 shows luciferase expression in human breast tumor xenografts (BT-474) in immunodeficient nude mice following peritumoral injection of GENOSPHERES or plasmid-liposome complexes. The experimental conditions are similar to that of Table 7. Although reporter gene was delivered locally at the tumor periphery, luciferase expression from traditional plasmid-liposome complexes (DDAB/Chol 12:12, nmol:nmol per micro-g DNA) in lung remained 30-fold higher than in tumor. In contrast, gene transfer mediated by GENOSPHERES of different lipid composition was higher in tumor in comparison with lung in every animal and the expression value in tumor ranged from 3- to 77-fold higher relative to expression mediated by traditional plasmid-liposome complexes.

TABLE 8

| Lipid composition | Luciferase expression (pg/mg tissue protein) | |
|---|---|---|
| (nmol lipid ratio/µg DNA) | tumor | lung |
| GENOSPHERES: | | |
| DDAB/CHIM/POPC (6:4.8:7.2) | 1.1 | 0.18 |
| DDAB/CHIM/POPC/mPEG-DSPE (6:4.8:7.2:0.12) | 0.44 | 0.21 |
| DDAB/Chol/POPC (6:6:6) | 0.34 | 0.13 |
| DDAB/Chol/POPC/mPEG-DSPE (6:6:6:0.12) | 7.74 | 0.16 |
| DDAB/CHEMS/POPC (6:3:9) | 0.56 | 0.22 |
| DDAB/CHEMS/POPC/mPEG-DSPE (6:3:9:0.12) | 1.55 | 0.80 |
| Plasmid-liposome complexes: | | |
| DDAB/Chol (12:12) | 0.10 | 3.30 |

Table 9 shows luciferase gene expression in H-157 human lung carcinoma xenografts in mice following peritumoral injection of GENOSPHERES of various composition. The experimental condition are the same as in Table 7. Three clear trends were seen in this series of experiments: (1) DOTAP is consistently better than DDAB; (2) inclusion of mPEG-DSPE decreases gene transfer; (3) lyophilization promotes gene transfer consistently both in lung and tumor by 2-5 fold.

TABLE 9

| Lipid composition | Luciferase expression (pg/mg tissue protein) | |
|---|---|---|
| (nmol lipid per micro-g DNA) | tumor | lung |
| GENOSPHERES: | | |
| DOTAP/CHIM/POPC (6:4.8:7.2) | 3.57 | 0.66 |
| DDAB/CHIM/POPC (6:4.8:7.2) | 2.8 | 0.15 |

TABLE 9-continued

| Lipid composition | Luciferase expression (pg/mg tissue protein) | |
|---|---|---|
| (nmol lipid per micro-g DNA) | tumor | lung |
| DDAB/CHIM/Chol/POPC/mPEG-DSPE (6:4.8:6:6:0.12) | 1.65 | 0.06 |
| DDAB/Chol/POPC/mPEG-DSPE (6:6:6:0.12) | 0.33 | 0.05 |
| GENOSHPHERES - lyophilized and reconstituted: | | |
| DOTAP/CHIM/POPC (6:4.8:7.2) | 22.60 | 5.62 |
| DDAB/CHIM/POPC (6:4.8:7.2) | 6.67 | 2.08 |

Table 10 shows luciferase expression in mouse tissues following intravenous administration of luciferase-encoding plasmid DNA formulated in GENOSPHERES or plasmid-liposome complexes to nude mice bearing subcutaneous xenografts of H-157 human lung carcinoma. The tumors were developed in immunodeficient nude mice according to the procedure of Table 7. The GENOSPHERES were injected intravenously at 100 micro-g DNA per mouse. Lyophilized GENOSPHERES of DDAB/CHIM/POPC, as well as plasmid-liposome complexes of DDAB/Cholesterol, generated high transfection activity in lung. Intravenous delivery of GENOSPHERES resulted in transfection of the tumor UD, undetectable.

TABLE 10

| Lipid composition | Luciferase expression (pg/mg tissue protein) | | | |
|---|---|---|---|---|
| (nmol lipid ratio/µg DNA) | lung | heart | liver | tumor |
| Plasmid-liposome complexes: | | | | |
| DDAB/Chol (12:12) | 631.0 | 8.1 | 0.14 | UD |
| GENOSPHERES (lyophilized and reconstituted): | | | | |
| DDAB/CHIM/POPC (6:4.8:7.2) | 12.9 | 0.1 | 0.04 | 0.15 |
| DOTAP/CHIM/POPC (6:4.8:7.2) | 379.0 | 0.6 | 0.06 | UD |

Example 16

Storage Conditions and Stability of GENOSPHERES

One mg of plasmid DNA was combined with the lipid mixture containing 6 micro-mol DDAB, 15 micro-mol POPC, 10 micro-mol Choesterol, and 0.21 micro-mol of DSPE-PEG (M.w. 2,000) in 2 mL of a monophase composed of equal parts of ethanol and 5% aqueous dextrose at 55° C. Ethanol was removed by extensive dialysis against 5 mM HEPES-Na buffer, pH 7.4 at room temperature. Final volume of the preparation was approximately 3.6 mL. This sample was divided into 0.2-mL aliquots to which and equal volumes of stock 10% (w/w) dextrose, 10% (w/w) sucrose, or 20% (w/w) sucrose were added. The samples were then stored in a liquid form at 4-6° C., or frozen at −80° C., or lyophilized overnight and stored in a solid form at 4-6° C. for 1 week. The frozen samples were then thawed at room temperature, and the lyophilized samples were reconstituted in water to original DNA concentration. The size of particles was determined by dynamic light scattering, and the DNA exposure was determined by the dye accessibility assay. These parameters were compared with the pre-storage value of particle size (weighted average±standard deviation (SD), 71.3 nm±29.3 nm), and dye accessibility 10.0%. The data are summarized in the following table:

TABLE 11

| Storage Condition | Cryoprotectant | Particle size, nm (average ± SD) | % Dye accessibility |
|---|---|---|---|
| +4° C. | 5% dextrose | 69.7 ± 29.5 | 10.9 |
| " | 5% sucrose | 70.5 ± 29.7 | 9.9 |
| " | 10% sucrose | 77.6 ± 30.9 | 14.2 |
| −80° C. | 5% dextrose | 72.0 ± 30.5 | 12.8 |
| " | 5% sucrose | 78.6 ± 30.5 | 11.0 |
| " | 10% sucrose | 74.1 ± 30.5 | 12.2 |
| Lyophilized | 5% dextrose | 72.0 ± 30.5 | 19.7 |
| " | 5% sucrose | 78.6 ± 30.5 | 16.5 |
| " | 10% sucrose | 74.1 ± 30.5 | 14.9 |

Example 17

Buoyant Density of GENOSPHERES and Liposomes

GENOSPHERES were prepared as described in Example 16, using the following lipid compositions (per 1 mg of plasmid DNA):

Composition 1: DDAB 6 micro-mol; POPC, 15 micro-mol, Cholesterol, 10 micro-mol; PEG (M.w. 2,000)-DSPE, 0.06 micro-mol.

Composition 2: DDAB 6 micro-mol; POPC, 25 micro-mol, Cholesterol, 6 micro-mol; CHEMS, 9 micro-mol; CHIM 1.67 micro-mol; PEG (M.w. 2,000)-DSPE, 0.06 micro-mol. Liposomes (without nucleic acid) having lipid composition 1 were prepared by the same procedure but with omission of the plasmid DNA.

Sucrose gradients were prepared by filling disposable polyallomer centrifuge tubes, 13×51 mm, with 4 mL of 15% (w/w) aqueous solution of sucrose, and subjecting the tubes to 5 cycles of freezing and thawing. Aliquots (0.2 mL) of the GENOSPHERES, DNA-free liposomes, or free plasmid DNA were applied on the top of the gradient tubes, and the tubes were centrifuged for 8 hours at 180,000×g at 20° C. The location of the particles was detected by light scattering upon tangential illumination of the tubes with a fiberoptic light source. The particles formed clearly defined bands. Sequential aliquots (fractions) of 0.2 mL were withdrawn from the gradients from the top down, and the fraction density was calculated from the sucrose concentration determined by refractometry, using the table from CRC Handbook of Chemistry and Physics, Edition 44. DNA in the fractions was determined by PicoGreem dye binding assay. Despite having different lipid composition, both GENOSPHERE samples were localized in the same gradient area having the density of 1.025-1.038, while DNA-free liposomes were localized at the density of 1.014-1.016. Free DNA was found in the fractions close to the bottom of the tubes.

Example 18

GENOSPHERES Containing PEG-PE Derivatives: DNA Encapsulation Filterability, and Targeted Transfection GENOSPHERES were prepared using the following lipid compositions (per 1 mg of plasmid DNA):

Composition 1: DOTAP 6 micro-mol; POPC, 15 micro-mol, Cholesterol, 10 micro-mol

Composition 2: DOTAP 6 micro-mol; POPC, 15 micro-mol; CHIM, 8 micro-mol; 1,2-dioleoylglycerol hemisuccinate (DOGHEMS) 2 micro-mol; DOPE, 2 micro-mol. Additionally, the compositions included various amounts (0-4 mol. % of total lipid) of PEG-lipids PEG-DMPE or PEG-DSPE (PEG mol. weight 2,000). The lipids were measured out from stock ethanol solutions and made up to 0.5 ml with 100% ethanol. To this solution, 0.5 ml of either 5 mM HEPES-Na buffer, pH 7.4 (Composition 1) or 5 mM MES-Na buffer, pH 5.5 (Composition 2 were added. Plasmid DNA (100 µg; containing luciferase reporter gene under the CMV promoter control) was made up to 0.5 ml in respective buffer solution, and mixed with 0.5 ml of 100% ethanol. Lipids and DNA solutions were incubated at 55° C. for 10 min, mixed at this temperature, and allowed to cool down to ambient temperature. After cooling, ethanol was removed by extensive dialysis against 144 mM NaCl at room temperature.

To obtain HER2-targeted formulations, aliquots of the preparations were incubated with the conjugate prepared from a highly internalizable anti-HER2 scFv antibody fragment F5Cys and maleimido-PEG-DSPE as described by Nielsen et al., 2002, at the ratio of 15 µg F5 protein per 1 µmole of phospholipid at 37° C. overnight. Equivalent amounts of PEG-DSPE were added to the control (non-targeted) preparations under the same conditions.

Samples of the formulations were passed under positive pressure through a surfactant-free cellulose acetate sterile filter with pore size of 0.45-µm. Filtering efficiency was calculated as the proportion of GENOSPHERE-encapsulated DNA that passed through the filter.

The degree of DNA exposure in the filtered samples was determined by PicoGreen® dye accessibility assay. Due to the low yields of the filtered particles in the samples without PEG-lipid, dye accessibility assay was not determined (n.d.) in these samples. The particle size was determined by dynamic light scattering using Nicomp C370 apparatus (Particle Size Systems) using solid particle Gaussian weight-average mode.

The transfection activity of GENOSPHERE-encapsulated plasmid DNA was determined in the cultures of HER2-over-expressing cells (SK-Br-3) using the protocol described under Characterization of GENOSPHERES, Section 5 above. Transfection efficiency was expressed as ng of luciferase produced per mg of total cell lysate protein.

The results are summarized in the following Table:

TABLE 12

| Composition and PEG-lipid | PEG-lipid, mol % | Particle size, nm (Mean ± SD) | % dye-accessible DNA | Filtering efficiency, % | Transfection activity, HER2-targeted | Transfection activity, non-targeted control |
|---|---|---|---|---|---|---|
| Composition 1: | | | | | | |
| None | N/A | 88.6 ± 34.6 | n.d. | 7.6 | 0.889 ± 1.130 | 0.015 ± 0.016 |
| PEG-DSPE | 0.25 | 79.5 ± 34.2 | 23.5 | 54.2 | 0.087 ± 0.015 | 0.007 ± 0.002 |
| PEG-DSPE | 0.50 | 63.8 ± 34.5 | 12.5 | 81.4 | 0.230 ± 0.041 | 0.016 ± 0.005 |

TABLE 12-continued

| Composition and PEG-lipid | PEG-lipid, mol % | Particle size, nm (Mean ± SD) | % dye-accessible DNA | Filtering efficiency, % | Transfection activity, HER2-targeted | Transfection activity, non-targeted control |
|---|---|---|---|---|---|---|
| PEG-DSPE | 1.0 | 70.5 ± 37.2 | 14.1 | 98.3 | 0.765 ± 0.072 | 0.026 ± 0.002 |
| PEG-DSPE | 2.0 | 65.4 ± 39.0 | 11.9 | 83.6 | 0.698 ± 0.175 | 0.022 ± 0.004 |
| PEG-DSPE | 4.0 | 59.1 ± 35.5 | 12.5 | 79.4 | 0.520 ± 0.09 | 0.004 ± 0.001 |
| PEG-DMPE | 0.25 | 74.5 ± 37.8 | 13.3 | 62.8 | 0.222 ± 0.022 | 0.009 ± 0.005 |
| PEG-DMPE | 0.5 | 94.6 ± 39.2 | 10.6 | 20.5 | 0.154 ± 0.037 | 0.013 ± 0.007 |
| PEG-DMPE | 1.0 | 85.8 ± 43.0 | 9.4 | 82.7 | 0.385 ± 0.069 | 0.008 ± 0.002 |
| PEG-DMPE | 2.0 | 90.3 ± 39.8 | 11.7 | 931 | 2.713 ± 1.926 | 0.009 ± 0.002 |
| PEG-DMPE | 4.0 | 102.2 ± 43.1 | 19.8 | 75.7 | 0.796 ± 0.171 | 0.037 ± 0.011 |
| Composition 2: | | | | | | |
| None | N/A | 75.8 ± 39.2 | n.d. | 10.5 | 4.345 ± 0.599 | 0.036 ± 0.008 |
| PEG-DSPE | 0.25 | 84.7 ± 40.9 | 5.9 | 70.4 | 3.077 ± 0.814 | 0.017 ± 0.002 |
| PEG-DSPE | 0.50 | 72.3 ± 36.7 | 5.3 | 93.4 | 4.337 ± 0.748 | 0.029 ± 0.005 |
| PEG-DSPE | 1.0 | 63.8 ± 37.3 | 6.6 | 86.1 | 2.029 ± 0.218 | 0.009 ± 0.002 |
| PEG-DSPE | 2.0 | 60.2 ± 38.0 | 7.9 | 87.5 | 1.475 ± 0.132 | 0.001 |
| PEG-DSPE | 4.0 | 85.4 ± 44.4 | 11.2 | 86.7 | 0.869 ± 0.114 | 0.001 |
| PEG-DMPE | 0.25 | 99.5 ± 44.4 | 7.0 | 77.7 | 4.143 ± 0.534 | 0.031 ± 0.014 |
| PEG-DMPE | 0.5 | 76.8 ± 38.4 | 7.9 | ≈100 | 4.410 ± 0.723 | 0.025 ± 0.010 |
| PEG-DMPE | 1.0 | 67.3 ± 36.8 | 8.0 | 91.5 | 3.073 ± 0.706 | 0.027 ± 0.009 |
| PEG-DMPE | 2.0 | 76.4 ± 39.2 | 9.7 | 82.9 | 3.170 ± 0.615 | 0.015 ± 0.003 |
| PEG-DMPE | 4.0 | 92.1 ± 31.9 | 8.9 | 90.1 | 0.936 ± 0.116 | 0.013 ± 0.001 |

Addition of PEG-lipid as low as 0.25 mol. % (of total phospholipid) dramatically increased the proportion of GENOSPHERES that passed through the 0.45-μm filter, while the particle size remained in the range of 60-100 nm, evidencing that PEG-lipid reduced the tendency of the particles for non-specific adsorption on surfaces. Formulations targeted with cell-internalizable anti-HER2 antibody fragment showed one to three orders of magnitude greater transgene expression in HER2-overexpressing cells than non-targeted ones.

Example 19

GENOSPHERES Prepared with Addition of Polyethoxylated Nonionic Detergent (TWEEN-60®)

GENOSPHERES encapsulating plasmid DNA into the lipid composition, per 1 weight part of DNA: DDAB 6 molar parts; POPC 15 molar parts; CHIM 8 molar parts; DOGHEMS 2 molar parts, and DOPE 2 molar parts, were prepared by combining equal volumes of the DNA solution in 1:1 mixture (by volume) of absolute ethanol and 5% aqueous dextrose, and the lipid solution in 1:1 mixture (by volume) of absolute ethanol and 5 mM HEPES-Na buffer pH 7.4 at 60° C. After combining of the DNA and lipid solutions, 10% (w/w) aqueous stock solution of a polyethoxylated non-ionic surfactant, poly(oxyethylene)sorbitan monostearate (trade name TWEEN-60) was added to the mixture to achieve molar ratio of TWEEN-60 to total lipid of 1:10. The mixture was allowed to reach ambient temperature, and was extensively dialyzed against 144 mM aqueous NaCl to remove ethanol. The DNA-lipid particles were produced having the size of 96.0±42.3 nm (mean±SD) as measured by dynamic light scattering as described elsewhere in this disclosure. The particles at the encapsulated DNA concentration of 20.6 mg/mL (*) were passed through the polyethersulfone filter with the pore size of 0.2 μm using positive pressure. The DNA concentration in the filtrate was 16.4 mg, signifying filtration efficiency of 79.6%. Thus, GENOSPHERES prepared with additional step of adding even a small amount of polyethoxylated non-ionic detergent (one-tenth of total lipid) were surprisingly more passable through a sterilizing filter, providing an important advantage in manufacturing.

Example 20

Effect of Exposure to Plasma on the GENOSPHERES Prepared with Addition of TWEEN

GENOSPHERES containing plasmid DNA and lipids, as indicated in the Table below (in molar parts of each lipid per one weight part DNA) were prepared as in Example D, except that in the case of GENOSPHERES containing DOGHEMS MES-Na buffer with pH 5.5 was substituted for HEPES-Na, pH 7.4. The preparations were sterilized by passage through 0.2 μm polyethersulfone sterile filters under positive pressure. Filter-sterilized preparations were aseptically mixed with equal volumes of human donor plasma clarified by centrifugation and 0.2 μm sterile filtration. The mixtures were incubated at 37° C.; aliquots were withdrawn 1, 24, and 49 hours later, and analyzed for particle size by DLS and for DNA exposure by PicoGreen® DNA-binding dye accessibility assay. Since the pure plasma showed presence of endogenous particles with size only less than 40 nm, the size distribution peaks having average size above 40 nm were attributed to GENOSPHERES. The data are summarized in the table below.

Composition 1: DOTAP 6; POPC 15; Chol 10
Composition 2. DOTAP 6, POPC 15; Chol 8; DOPE 2
Composition 3: DOTAP 6; POPC 15; Chol 8; DOGHEMS 2; DOPE 2

TABLE 13

| Composition | Incubation time, hours | Particle size, mean ± SD (nm) | % dye-accessible DNA |
|---|---|---|---|
| 1 | 0 | 127.55 ± 3.46 | 16.56 ± 0.71 |
| 1 | 1 | 722.83 ± 66.59 | 21.56 ± 0.96 |
| 1 | 24 | 381.53 ± 350.42 | 18.94 ± 0.42 |
| 1 | 48 | 196.67 ± 74.19 | 18.26 ± 0.67 |
| 2 | 0 | 59.65 ± 0.63 | 10.02 ± 0.36 |
| 2 | 1 | 453.97 ± 196.67 | 11.81 ± 0.61 |

TABLE 13-continued

| Composition | Incubation time, hours | Particle size, mean ± SD (nm) | % dye-accessible DNA |
|---|---|---|---|
| 2 | 24 | 792.6 ± 25.03 | 8.60 ± 0.33 |
| 2 | 48 | 361.6 ± 103.51 | 11.9 ± 0.50 |
| 3 | 0 | 90.90 ± 4.52 | 16.36 ± 0.68 |
| 3 | 1 | 113.83 ± 19.75 | 6.57 ± 0.24 |
| 3 | 24 | 119.30 ± 39.90 | 6.84 ± 0.19 |
| 3 | 48 | 124.20 ± 11.05 | 7.46 ± 0.34 |

A degree of particle aggregation was noticed in plasma in compositions 1 and 2, but composition 3 that contained negatively charged, pH titratable lipid DOGHEMS was surprisingly more stable against aggregation in plasma. 3. In all three compositions, particles were stable against disintegration as evidenced by the absence of increase in DNA exposure.

Example 21

Transfection Activity of GENOSPHERES Prepared with Addition of TWEEN

GENOSPHERES containing plasmid DNA encoding luciferase reporter gene and the following lipids (molar parts per one weight part of DNA): DOTAP 6; POPC 15; Cholesterol 8; DOGHEMS 2; DOPE 2 were prepared as described in Example 20 above. The size of resulting DNA-lipid particles was 83.2±41.8 nm (mean±SD) by dynamic light scattering. HER2-targeted GENOSPHERES formulation was obtained by incubation of the particles with the conjugate of anti-HER2 scFv antibody fragment F5Cys and maleimido-PEG-DSPE as described by Nielsen et al., 2002, at the ratio of 15 µg F5 protein per 1 µmole of phospholipid at 57° C. for 1 hour. The GENOSPHERES were sterilized by passage through 0.2 um polyethersulfone filter, and assayed for DNA exposure by dye accessibility assay and for transfection activity in HER2-overexpressing breast carcinoma cells (SK-BR-3) as described elsewhere in this disclosure. The results are summarized in the following table:

TABLE 14

| Formulation | Dye-accessible DNA, % | Filtration efficiency, % | Transgene expression, ng luciferase/mg cell protein |
|---|---|---|---|
| Non-targeted | 23.14 ± 0.96 | 72.6 | 1.04 ± 0.156 |
| HER2-targeted | 24.92 ± 0.45 | 78.8 | 0.04 ± 0.019 |

Example 22

Characterization of GENOSPHERES Containing pH Titratable Lipids

GENOSPHERES containing cationic, neutral, and pH titratable lipids were prepared by combining equal volumes of plasmid DNA solution in ethanol/5% aqueous dextrose 1:1 (by volume) and the lipids, as indicated under Formulation in the Table below, in the same solvent mixture, at 58° C., followed by removal of ethanol by vacuum evaporation at the same temperature and subsequent dialysis against 5 mM HEPES-Na, 5% sucrose, pH 7.0, or 5 mM MES-Na, 5% sucrose, pH 5.5, as indicated. Particle sizes were determined by dynamic light scattering. Surface potential of the particles (zeta-potential) was determined from their electrophoretic mobility in the above buffers additionally containing 5 mM NaCl using dynamic light scattering device (Zeta-Sizer, Malvern). The results are summarized in the following table (n.d.—not determined):

TABLE 15

| Formulation (molar parts per one weight part of DNA) | Particle size, nm (volume average) | Zeta-potential, mV | |
|---|---|---|---|
| | | pH 7.0 | pH 5.5 |
| DOTAP 5; POPC 25; Chol 6; CHEMS 9; CHIM 1.67 | 113.8 | −25.1 ± 0.4 | +15.2 ± 0.8 |
| DOTAP 6; POPC 25; Chol 6; CHEMS 8; CHIM 2.67 | 89.0 | −20.0 ± 0.6 | +19.5 ± 0.2 |
| DOTAP 5; POPC 25; Chol 16.7; DOGHEMS 6 | 150 | −15.7 ± 0.3 | +20.2 ± 0.8 |
| DOTAP 5; POPC 15; Chol 5; CHEMS 5; CHIM 1 | 82.7 | ~0 | +35.5 ± 1.3 |
| DOTAP 5; POPC 25; Chol 7; CHEMS 6; CHIM 3.67 | 88.2 | −2 | +42.2 ± 0.3 |
| DOTAP 6; POPC 18; Chol 6; CHEMS 5; CHIM 1 | 81.1 | −4 | +41.6 ± 0.5 |
| DOTAP 6; POPC 25; Chol 7; CHEMS 6; CHIM 3.67 | 88.9 | ~0 | +46.6 ± 0.8 |
| DDAB 6; POPC 15; Chol 10 | 82.0 | +54.4 ± 0.1 | n.d. |
| DOTAP 6; POPC 15; Chol 10 | 93.8 | +57.3 ± 0.8 | n.d. |

GENOSPHERES containing ph-titratable anionic lipids, such as CHEMS and DOGHEMS, along with cationic lipids, while being anionic or nearly neutral at neutral pH, acquired positive charge when exposed to lower pH (pH 5.5) characteristic for cellular endosomes and lysosomes.

Example 23

Using Light Scattering and Particle Size Analysis in Determining Molecular or Micellar Character of the Solution Particle-forming component consisting of the following lipids: DOTAP 6 molar parts, POPC 15 molar parts, Cholesterol 10 molar parts, and PEG-DSPE (PEG Mol. weight 2000) 0.16 molar parts, was dissolved in ethanol-water mixture 1:1 by volume and filtered through 0.2 µm membrane filter with the pore size of 0.2 µm to remove dust and particulate contaminants. The filtrate was lyophilized and redissolved in 5% aqueous dextrose containing various volume percentages of ethanol to achieve total lipid concentration of 2.1 mM. The solution was placed in a thermostatted cuvette using Nicomp C370 dynamic light scattering particle size analyzer (Particle Size Systems, Inc.) and equilibrated at 55° C. and then at 23° C. The light scattering intensity was estimated from the photon count frequency recorded at constant amplifier gain throughout the experiment. The particle size was determined using quasielastic light scattering in a Gaussian approximation mode (for chi-square factor of less than 3) or Nicomp size distribution analysis algorhythm (for chi-square factor of 3 or more) for vesicles, and expressed as volume-average mean diameter±standard deviation, or as mean diameter followed by relative mass fraction (%) for every histogram peak, respectively. The viscosity and refraction index values necessary for the particle size calculations were determined by drop-ball viscometry and from the published ethanol-water refraction index tables, respectively. The results are summarized in the following table:

TABLE 16

| Ethanol, | Photon counting rate, kHz | | Particle size, nm | |
|---|---|---|---|---|
| vol. % | at 55° C. | at 23° C. | at 55° C. | at 23° C. |
| 30 | 350 | 160 | 99.0 ± 45.2 | 12.1; 20.55% |
|  |  |  |  | 65.3; 55% |
|  |  |  |  | 348.0; 24.4% |
| 40 | 460 | 1100 | 201.9 ± 54.1 | 209.9 ± 45.7 |
| 50 | 11 | 900 | N.d. | 11.4; 5.4% |
|  |  |  |  | 159.1; 2.4% |
|  |  |  |  | 980.0; 92.3% |
| 60 | 2 | 320 | N.d. | 56.8; 3.7% |
|  |  |  |  | 562.3; 30.1% |
|  |  |  |  | 1855.5; 66.2% |

At 55° C. and ethanol content over 40 vol. %, the intensity of light scattering dropped dramatically, and the particle size was undeterminable, signifying that under these conditions and without NAC the particulate condensed phases were absent, that is, PFC was molecularly or micellarly dissolved.

Although the invention has been described with respect to particular embodiments, it will be apparent to those skilled in the art that various changes and modifications can be made without departing from the invention. The scope of the invention should, therefore, be determined with the full scope of equivalents pertaining thereto. The disclosures of all articles and references, including patent applications and publications, are incorporated herein by reference for all purposes.

The subject matter claimed is:

1. A process for preparing a microparticulate complex of a nucleic acid component and a lipid composition, which process comprises:

combining, at a temperature of from 30° to 80° C., the lipid composition, said lipid composition comprising cationic and non-cationic lipids, and the nucleic acid component in an aqueous/organic solvent system consisting essentially of a single liquid phase comprising water and a water-miscible organic solvent in an amount from 40% to about 55% by volume of said liquid phase to form a mixture wherein the lipid composition and the nucleic acid component are independently molecularly or micellarly soluble in said liquid phase, and wherein said organic solvent is an alcohol and is essentially free from a halogenated hydrocarbon, and the ionic strength of the solvent system is less than that of about 50 mM NaCl whereby a monophasic system is formed, and reducing the amount of the organic solvent in the monophasic system, whereby the formation of the microparticulate complex of the nucleic acid component and the lipid composition occurs.

2. The process of claim 1, wherein the water-miscible organic solvent is ethanol.

* * * * *

UNITED STATES PATENT AND TRADEMARK OFFICE
CERTIFICATE OF CORRECTION

| | | |
|---|---|---|
| PATENT NO. | : 8,496,961 B2 | Page 1 of 1 |
| APPLICATION NO. | : 10/439856 | |
| DATED | : July 30, 2013 | |
| INVENTOR(S) | : Hong et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1833 days.

Signed and Sealed this
Seventeenth Day of March, 2015

Michelle K. Lee
*Director of the United States Patent and Trademark Office*